US009045554B2

(12) United States Patent
Olson

(10) Patent No.: US 9,045,554 B2
(45) Date of Patent: *Jun. 2, 2015

(54) RIBONUCLEIC ACID BINDING MOTIF PROTEIN 20 SEQUENCE VARIANTS

(71) Applicant: Mayo Foundation for Medical Education and Research, Rochester, MN (US)

(72) Inventor: Timothy M. Olson, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/032,043

(22) Filed: Sep. 19, 2013

(65) Prior Publication Data

US 2014/0039174 A1    Feb. 6, 2014

Related U.S. Application Data

(63) Continuation of application No. 13/105,669, filed on May 11, 2011, now Pat. No. 8,563,705.

(60) Provisional application No. 61/334,022, filed on May 12, 2010.

(51) Int. Cl.
| | | |
|---|---|---|
| C07K 14/47 | (2006.01) | |
| C07H 21/02 | (2006.01) | |
| C07H 21/04 | (2006.01) | |
| A61B 5/00 | (2006.01) | |
| C12Q 1/68 | (2006.01) | |

(52) U.S. Cl.
CPC .............. *C07K 14/47* (2013.01); *A61B 5/0071* (2013.01); *C12Q 1/6883* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 5,451,683 | A | 9/1995 | Barret et al. |
| 5,733,729 | A | 3/1998 | Lipshutz et al. |
| 5,770,772 | A | 6/1998 | Aono et al. |
| 8,563,705 | B2 | 10/2013 | Olson |
| 2006/0263805 | A1 | 11/2006 | Terzic et al. |
| 2012/0277282 | A1 | 11/2012 | Gotthardt et al. |

FOREIGN PATENT DOCUMENTS

| WO | WO 98/20019 | 5/1998 |
| WO | WO 99/57318 | 11/1999 |

OTHER PUBLICATIONS

Brauch et al., "Mutations in ribonucleic acid binding protein gene cause familial dilated cardiomyopathy," *J Am Coll Cardiol.*, 54(10):930-941, Sep. 2009.

Cole et al., Monoclonal Antibodies and Cancer Therapy, Alan R. Liss, Inc., pp. 77-96, 1983.
Correlagen®, "CardioGeneScan: Familial Cardiomyopathy—an Overview," <URL: https://www.correlagen.com/fields/other/reviews/FCA_CRLGOvw.pdf>, 11 pages, copyright 2010.
Correlagen®, "Facts on Familial Dilated Cardiomyopathy (DCM)," <URL: https://www.correlagen.com/fields/cardiology/downloads/DCM_facts.pdf>, 1 page, copyright 2007, 2009.
Correlagen®, CardioGeneScan: Using Genetic Testing to Diagnose Familial Cardiomyopathy, 2 pages, copyright 2010.
Cote et al. "Generation of human monoclonal antibodies reactive with cellular antigens," *Proc. Natl. Acad. Sci USA* 80(6):2026-2030, Apr. 1983.
Desai et al., "Implantable defibrillators for the prevention of mortality in patients with nonischemic cardiomyopathy: a meta-analysis of randomized controlled trials," *JAMA*, 292(23):2874-2879, Dec. 2004.
Fowler et al., "The genetics of cardiomyopathy: Genotyping and genetic counseling," *Curr. Treatment Options in Cardiovasc. Med.*, 11:433-446 , 2009.
GenBank Accession No. BAE24961; GI No. 74209138, "unnamed protein product [*Mus musculus*]," 3 pages, Sep. 2008.
GenBank Accession No. CAG01297; GI No. 47214762, "unnamed protein product [*Tetraodon nigroviridis*]," 1 page, Mar. 2004.
GenBank Accession No. NC_000010.10; GI No. 224589801, "*Homo sapiens* chromosome 10, GRCh37 primary reference assembly," 2 pages, Jun. 2009.
GenBank Accession No. NM_001134363.1; GI No. 197276593, "*Homo sapiens* RNA binding motif protein 20 (RBM20), mRNA," 4 pages, Mar. 2009.
GenBank Accession No. NP_001101081; GI No. 255982592, "RNA-binding protein 20 [*Rattus norvegicus*]," 1 page, Aug. 2009.
GenBank Accession No. NP_001127835.1; GI No. 197276594, "RNA-binding protein 20 [*Homo sapiens*]," 1 page, Mar. 2009.
GenBank Accession No. XP_421755; GI No. 118093031, "Predicted: hypothetical protein [*Gallus gallus*]," 1 page, Nov. 2006.
GenBank Accession No. XP_50832; GI No. 114632917, "Predicted: hypothetical protein [*Pan troglodytes*]," 1 page, Sep. 2006.
GenBank Accession No. XP_544017; GI No. 57107611, "Predicted: similar to 1110018J23Rik protein [*Canis familiaris*]," 2 pages, Jan. 2005.
GenBank Accession No. XP_603772; GI No. 194678822, "Predicted: similar to hCG2036763 [*Bos taurus*]," 1 page, Jul. 2008.
GenBank Accession No. XP_683222; GI No. 125851038, "Predicted: similar to RNA binding motif protein 20 [*Danio rerio*]," 1 page, Jul. 2008.
GeneDx, "Dilated Cardiomyopathy: A Guide for Clinicians," <URL: http://www.genedx.com/wp-content/uploads/crm_docs/90346-clinician-guide-dcm-.pdf>, 12 pages, copyright 2012.
GeneDx, Test Information Sheet, "Cardiology Genetics: Dilated Cardiomyopathy (DCM)/ Letft Ventricular Noncompaction (LVNC) Panel," <URL: http://www.genedx.com/wp-content/uploads/crm_docs/info_sheet_dcm.pdf>, 2 pages, updated Jun. 2012.

(Continued)

*Primary Examiner* — Carla Myers
(74) *Attorney, Agent, or Firm* — Fish & Richardson P.C.

(57) ABSTRACT

This document relates to methods and materials for using nucleic acid and amino acid sequence variants of ribonucleic acid binding motif protein 20 (RBM20). For example, methods and materials for using nucleic acid sequence variants and/or their corresponding amino acid variants of RBM20 that are associated with dilated cardiomyopathy to identify mammals (e.g., humans) at risk of having dilated cardiomyopathy that is likely to progress to heart failure are provided.

2 Claims, 8 Drawing Sheets

(56) References Cited

OTHER PUBLICATIONS

Guatelli et al., "Isothermal, in vitro amplification of nucleic acids by a multienzyme reaction modeled after retroviral replication," *Proc. Natl. Acad. Sci. USA*, 87(5):1874-1878, Mar. 1990.

Hacia et al., "Detection of heterozygous mutations in BRCA1 using high density oligonucleotide arrays and two-colour fluorescence analysis," *Nature Genet.* 14(4):441-447, 1996.

Henry, et al., "Echocardiographic measurements in normal subjects from infancy to old age," *Circ.*, 62:1054-1061, 1980.

Hershberger and Morales "Dilated cardiomyopathy overview," Pagon et al., Eds., GeneReviews, 12 pages, Initial posting: Jul. 2007.

Hershberger et al., "Genetic evaluation of cardiomyopathy—a Heart Failure Society of America practice guideline," *J Card Fail.*, 15(2):83-97, Mar. 2009.

Huse et al., "Generation of a large combinatorial library of the immunoglobulin repertoire in phage lambda," *Science*, 246(4935):1275-1281, 1989.

Hyrup and Nielsen, "Peptide nucleic acids (PNA): synthesis, properties and potential applications," *Bioorgan. Med. Chem.* 4(1):5-23, Jan. 1996.

Köhler and Milstein, "Continuous cultures of fused cells secreting antibody of predefined specificity," *Nature* 256(5517):495-497, Aug. 1975.

Kozbor and Roder, "The production of monoclonal antibodies from human lymphocytes," *Immunology Today* 4(3):72-79, Mar. 1983.

Lewis, *Genetic Engineering News* 12(9):1, 1992.

Michels et al., "The frequency of familial dilated cardiomyopathy in a series of patients with idiopathic dilated cardiomyopathy," *N. Eng. J. Med.*, 326(2):77-82, Jan. 1992.

Myakishev et al. "High-throughput SNP genotyping by allele-specific PCR with universal energy-transfer-labeled primers," *Genome Res.* 11(1):163-169, Jan. 2001.

Prince et al. "Robust and accurate single nucleotide polymorphism genotyping by dynamic allele-specific hybridization (DASH): design criteria and assay validation," *Genome Res.*, 11:152-162, Jan. 2001.

Redfield et al., "Burden of systolic and diastolic ventricular dysfunction in the community: appreciating the scope of the heart failure epidemic," *JAMA* 289(2):194-202, Jan. 2003.

Schafer and Hawkins, "DNA variation and the future of human genetics," *Nat. Biotechnol.*, 16(1):33-39, 1998.

Stoneking et al. "Population variation of human mtDNA control region sequences detected by enzymatic amplification and sequence-specific oligonucleotide probes," *Am J Hum Genet.*, 48(2):370-382, Feb. 1991.

Summerton and Weller, "Morpholino antisense oligomers: design, preparation, and properties," *Antisense Nucleic Acid Drug Dev.* 7(3):187-195, Jun. 1997.

Underhill et al. "Detection of numerous Y chromosome biallelic polymorphisms by denaturing high-performance liquid chromatography," *Genome Res.*, 7(10):996-1005, Oct. 1997.

Weiss, "Hot prospect for new gene amplifier," *Science*, 254(5036):1292-3, Nov. 1991.

Wong et al. "Human GM-CSF: molecular cloning of the complementary DNA and purification of the natural and recombinant proteins," *Science*, 228(4701):810-815, May 1985.

Figure 1 – Partial RBM20 Gene Sequence

```
            ... TACGTGGTTT TCCTGTGTTT GGGAACTTAA TGAAAAAATG CCCATCCTTT
TAGAATATCG GATATATGAC TCAGTTGACC TGCTTAATAA CCAAACAGCC TTCAGAGTGT
ATCTGTATAT ATGTGCGTAT ATCTTTGTAC GTAACTGTTC AGGCTGGGAA TCTTTATTTG
TTTATTAGTC TGTCTGTTTT TTTAAAAAAA TTCTGATTAT TTGGGTTTTT TAAAGACGTG
TAAAGCCACA TCTTGCCACC TGCAATTCTG CGGCAGAGTG GAGGGGGGTT AGGAAGTCTT
GTTCTGAACC TTACACAGGT TGGGGTCCTT GTCTGGGTTT CAGTTTCTTC ATCTCAGACG
TGTAGATCAG GATTCTAGAG TATCTTCCAA CCCTAAAATG CCTTCCTAAT TCTTTTTTTT
AACCTCTGAG CGTGCCCTCC CCAATAGTTA GCATCCCTTT TCCATGCATA AATTGAGCTG
AGAAATAAAT GAGAAACTG GAGGCTAAGA GGTTGGCTTC ATTCTGATAC AGCCCAAATG
TAGGAGTGGC TTCAAGTCTT GTAGCTAAGA GGCCGGCTAA TGGCACCCAG GGTTAGGCAG
CCTTACCCAC TAGGCTGGAC TAGGGCAATC TTGCCCCCCA GCGCCCACCC CGCACACCCC
CAGGAGGAGA GTCAGAGGTC CGCTCCCTGA GCATAGCTCC CTTCCAAGAG AAGGCAAGCT
GGAACCGAGC CAAATCAGCC CAGTTCTTCT TCCTAGTTCC CAGGAGCAGA ATGAGTAAAG
GCACAGCGAG TGGCCAGTGC TGTGCTTAGG AGAAGTCCTC TGCACGGAAG CCAGAAGGGA
GGAAAAGGCT TTCTCCTGAA CCACTCTGTG TGGTTCTGTA GAGTTGGGAG TTAAGAGTGT
ACACAGTTAC ATGCACAGTA TATCTAAGAC AGAGACTGTG TGTCTGTGTG TGGGTGGGGT
GGGATGGGAG GTGTGAAGAT TCTAAATCCT GCTCCTTGGC TCCCTCACAG ATATGGCCCA
GAAAGGCCGC GGTCTCGTAG TCCGGTGAGC CGGTCACTCT CCCCGAGGTC CCACACTCCC
AGCTTCACCT CCTGCAGCTC TTCCCACAGC CCTCCGGGCC CCTCCCGGGC TGACTGGGGC
AATGGCCGGG ACTCCTGGGA GCACTCTCCC TATGCCAGGA GGGAGGAAGA GCGAGACCCG
GCTCCCTGGA GGGACAACGG AGATGACAAG AGGGACAGGA TGGACCCCTG GCACATGAT
CGCAAACACC ACCCCCGGCA ACTGGACAAG GCTGAGTTGG ACGAGCGACC AGAAGGAGGG
AGGCCCCACC GGGAGAAGTA CCCGAGATCT GGGTCTCCCA ACCTGCCCCA CTCTGTGTCC
AGCTACAAAA GCCGTGAAGA CGGCTACTAC CGGAAAGAGC CCAAAGCCAA GTGGGACAAG
TATCTGAAGC AGCAGCAGGA TGCCCCCGGG AGGTCCAGGA GGAAAGACGA GGCCAGGCTG
CGGGAAAGCA GACACCCCCA TCCGGATGAC TCAGGCAAGG AAGATGGGCT GGGGCCAAAG
GTCACTAGGG CCCCTGAGGG CGCCAAGGCC AAGCAGAATG AGAAAAATAA AACCAAGAGA
ACTGATAGAG ACCAAGAAGG AGCTGATGAT AGAAAAGAAA ACACAATGGC AGAGAATGAG
GTAATGATCA ATTTCTTCCC CAGGTAAGGC GAGGCAGGCC CTGAAGGAGA ATAATCATAA
TAATATAATG AGGATGAACG TTTATTGAAT GAATGAACAT TTACTGGCTA TTTACTATGC
GCTAGGCACT GTGCAAGACA CTTTATCTCA ATGAACTCAT TTAATCCTCA CAGGTTTTGA
GTACCAACCT TTGAGCTTGG TACTATTGTT ACTGCAGGTG AGGAGACTGA GGCACAGAGA
ACTTACGTTA TTTGTCCAAG AACACACGGT CAGGAAATGG CAGACCCAGA ATTATACCAA
GGAGATCTGG CCCCAAATCC CATGGCACCT GTTGCCTTTA CTAGAAGTTA GGGTGGGACA
TCATGGAAAG GCCTGTAGTC CTGTTCGTCC AGTAGGGAGT GGCCTGAGGT GTTTGCACCC
AAAGAGCCTC CCAAGGGAGA TTAGATCTTT GGTTCATTCT GTCCTCCCTC CTGCCAGAAG
CATTTACCAG TCCTGGAACT CTGAGGAGAA GTGGTGAAGG AGAAGCCGTC ACCACCTGCT
AAATTAAACT GGGTGCCCAG AGCTGTCCAC AGTGTTTTAC CTCCACTCTA ATAAAAATGC
ACGGTGGCTG GGCACAGTGG CTCATGCCTG TAATCCTAGC ACTTTGGGAG GCCGAGGCAG
GCAGATCACC TGAGGTCAGG AGTTCGAGAC CAGCCTGGCC AATATGGTGA AACCCTGTCT
CTACTAAAAA TACAAAAATT AGCCAGGCAA GGTGGTGCAC CCCTGTAGTC CCAGCTACTC
AGGAGGCTGA GGCAGGAGAA TCACTTTAAC CCGGAAGGCG GAGGTTGCAG TGAGCCGAGA
TCATGTCTTT GCACTCCAGC CTGGATGACA AGAGCGAAAC TCTATTTCAA AAAAAAAAAA
AAAAAAAAAA ATGCATGGCA ATGGCTGGCA CCTTCATGGC ATCTGAAAGG TCTGAGGGCT
TGCAGCAGTA CTTCAGTTCA CACAGGGGCG TCACAAGGAG ...
```

Figure 2, page 1 – RBM20 Coding Sequence

```
1     ATGGTGCTGG CAGCAGCCAT GAGCCAGGAC GCGGACCCCA GCGGTCCGGA GCAGCCGGAC
61    AGAGTTGCCT GCAGTGTGCC TGGTGCCCGG GCGTCCCCGG CACCCTCCGG CCCGCGAGGG
121   ATGCAGCAGC CGCCGCCGCC GCCCCAGCCA CCGCCCCCGC CCAAGCCGG CCTACCCCAG
181   ATCATCCAAA ATGCCGCCAA GCTCCTGGAC AAGAACCCAT TCTCGGTCAG TAACCCGAAC
241   CCTCTGCTTC CTTCACCTGC CAGTCTCCAG CTGGCTCAAC TGCAGGCCCA GCTCACCCTC
301   CACCGGCTGA AGCTGGCACA GACAGCTGTC ACCAACAACA CTGCAGCCGC CACAGTCCTG
361   AACCAAGTCC TCTCCAAAGT GGCCATGTCC CAGCCTCTCT TCAATCAACT GAGGCATCCG
421   TCTGTGATCA CTGGCCCCCA CGGCCATGCT GGGGTTCCCC AACATGCTGC AGCCATACCC
481   AGTACCCGGT TTCCCTCTAA TGCAATTGCC TTTTCACCCC CCAGCCAGAC ACGAGGCCCC
541   GGACCCTCCA TGAACCTTCC CAACCAGCCA CCCAGTGCCA TGGTGATGCA TCCTTTCACT
601   GGGGTAATGC CTCAGACCCC TGGCCAGCCA GCAGTCATCT TGGGCATTGG CAAGACTGGG
661   CCTGCTCCAG CTACAGCAGG ATTCTATGAG TATGGCAAAG CCAGCTCTGG CCAGACATAT
721   GGCCCTGAAA CAGATGGTCA GCCTGGCTTC CTGCCATCCT CGGCCTCAAC CTCGGGCAGT
781   GTGACCTATG AAGGGCACTA CAGCCACACA GGGCAGGATG GTCAAGCTGC CTTTTCCAAA
841   GATTTTTACG GACCCAACTC CCAAGGTTCA CATGTGGCCA GCGGATTTCC AGCTGAGCAG
901   GCTGGGGGCC TGAAAAGTGA GGTCGGGCCA CTGCTGCAGG GCACAAACAG CCAATGGGAG
961   AGCCCCCATG GATTCTCGGG CCAAAGCAAG CCTGATCTCA GCAGGTCC CATGTGGCCT
1021  CCACCCCACA ACCAGCCCTA TGAGCTGTAC GACCCCGAGG AACCAACCTC AGACAGGACA
1061  CCTCCTTCCT TCGGGGGTCG GCTTAACAAC AGCAAACAGG GTTTTATCGG TGCTGGGCGG
1141  AGGGCCAAGG AGGACCAGGC GTTGCTATCT GTGCGGCCCC TGCAGGCTCA TGAGCTGAAC
1201  GACTTTCACG GTGTGGCCCC CCTCCACTTG CCGCATATCT GTAGCATCTG TGACAAGAAG
1261  GTGTTTGATT TGAAGGACTG GGAGCTGCAT GTGAAGGGA AGCTGCACGC TCAGAAATGC
1321  CTGGTCTTCT CTGAAAATGC TGGCATCCGG TGTATACTTG GTTCGGCAGA GGGAACATTG
1381  TGTGCTTCTC CCAACAGCAC AGCTGTTTAT AACCCTGCTG GGAATGAAGA TTATGCCTCA
1441  AATCTTGGAA CATCATACGT GCCCATTCCA GCAAGGTCAT TCACTCAGTC AAGCCCCACA
1501  TTTCCTTTGG CTTCTGTGGG GACAACTTTT GCACAGCGGA AGGGGCTGG CCGTGTGGTG
1561  CACATCTGCA ATCTCCCTGA AGGAAGCTGC ACTGAGAATG ACGTCATTAA CCTGGGGCTG
1621  CCCTTTGGAA AGGTCACTAA TTACATCCTC ATGAAGTCGA CTAATCAGGC CTTTTTAGAG
1681  ATGGCTTACA CAGAAGCTGC ACAGGCCATG GTCCAGTATT ATCAAGAAAA ATCTGCTGTG
1741  ATCAATGGTG AGAAGTTGCT CATTCGGATG TCCAAGAGAT ACAAGGAATT GCAGCTCAAG
1801  AAACCCGGGA AGGCCGTGGC TGCCATCATC CAGGACATCC ATTCCCAGAG GGAGAGGGAC
1861  ATGTTCCGGG AAGCAGACAG ATATGGCCCA GAAAGGCCGC GGTCTCGTAG TCCGGTGAGC
1921  CGGTCACTCT CCCCGAGGTC CCACACTCCC AGCTTCACCT CCTGCAGCTC TTCCCACAGC
1981  CCTCCGGGCC CCTCCCGGGC TGACTGGGGC AATGGCCGGG ACTCCTGGGA GCACTCTCCC
2041  TATGCCAGGA GGGAGGAAGA GCGAGACCCG GCTCCCTGGA GGGACAACGG AGATGACAAG
2101  AGGGACAGGA TGGACCCCTG GCACATGAT CGCAAACACC ACCCCCGGCA ACTGGACAAG
2161  GCTGAGTTGG ACGAGCGACC AGAAGGAGGG AGGCCCCACC GGGAGAAGTA CCCGAGATCT
2221  GGGTCTCCCA ACCTGCCCCA CTCTGTGTCC AGCTACAAAA GCCGTGAAGA CGGCTACTAC
2281  CGGAAAGAGC CCAAAGCCAA GTGGGACAAG TATCTGAAGC AGCAGCAGGA TGCCCCCGGG
2341  AGGTCCAGGA GGAAAGACGA GGCCAGGCTG CGGGAAAGCA GACACCCCA TCCGGATGAC
2401  TCAGGCAAGG AAGATGGGCT GGGGCCAAAG GTCACTAGGG CCCCTGAGGG CGCCAAGGCC
2461  AAGCAGAATG AGAAAAATAA AACCAAGAGA ACTGATAGAG ACCAAGAAGG AGCTGATGAT
2521  AGAAAAGAAA ACACAATGGC AGAGAATGAG GCTGGAAAAG AGGAACAGGA GGGCATGGAA
2581  GAAAGCCCTC AATCAGTGGG CAGACAGGAG AAAGAAGCAG AGTTCTCTGA TCCGGAAAAC
```

Figure 2, continued - RBM20 Coding Sequence

```
2641 ACAAGGACAA AGAAGGAACA AGATTGGGAG AGTGAAAGTG AGGCAGAGGG GGAGAGCTGG
2701 TATCCCACTA ACATGGAGGA GCTGGTGACA GTGGACGAGG TTGGGGAAGA AGAAGATTTT
2761 ATCGTGGAAC CAGACATCCC AGAGCTGGAA GAAATTGTGC CCATTGACCA GAAAGACAAA
2821 ATTTGCCCAG AAACATGTCT GTGTGTGACA ACCACCTTAG ACTTAGACCT GGCCCAGGAT
2881 TTCCCCAAGG AAGGAGTCAA GGCCGTAGGG AATGGGGCTG CAGAAATCAG CCTCAAGTCA
2941 CCCAGAGAAC TGCCCTCTGC TTCCACAAGC TGTCCCAGTG ACATGGACGT GGAAATGCCT
3001 GGCCTAAATC TGGATGCTGA GCGGAAGCCA GCTGAAAGTG AGACAGGCCT CTCCCTGGAG
3061 GATTCAGATT GCTACGAGAA GGAGGCAAAG GGAGTGGAGA GCTCAGATGT TCATCCAGCC
3121 CCTACAGTCC AGCAAATGTC TTCCCCTAAG CCAGCAGAGG AGAGGGCCCG GCAGCCAAGC
3181 CCATTTGTGG ATGATTGCAA GACCAGGGGG ACCCCCGAAG ATGGGGCTTG TGAAGGCAGC
3241 CCCCTGGAGG AGAAAGCCAG CCCCCCCATC GAAACTGACC TCCAAAACCA AGCTTGCCAA
3301 GAAGTGTTGA CCCCGGAAAA CTCCAGGTAC GTGGAAATGA AATCTCTGGA GGTGAGGTCA
3361 CCAGAGTACA CTGAAGTGGA ACTGAAACAG CCCCTTTCTT TGCCCTCTTG GGAACCAGAG
3421 GATGTGTTCA GTGAACTTAG CATTCCTCTA GGGGTGGAGT TCGTGGTTCC CAGGACTGGC
3481 TTTTATTGCA AGCTGTGTGG GCTGTTCTAC ACGAGCGAGG AGACAGCAAA GATGAGCCAC
3541 TGCCGCAGCG CTGTCCACTA CAGGAACTTA CAGAAATATT TGTCCCAGCT GGCCGAGGAG
3601 GGCCTCAAGG AGACCGAGGG GGCAGATAGC CCGAGGCCAG AGGACAGCGG AATCGTGCCA
3661 CGCTTCGAAA GGAAAAAGCT CTGA
```

Figure 3 – RBM20 Amino Acid Sequence

```
1    MVLAAAMSQD ADPSGPEQPD RVACSVPGAR ASPAPSGPRG MQQPPPPPQP PPPPQAGLPQ
61   IIQNAAKLLD KNPFSVSNPN PLLPSPASLQ LAQLQAQLTL HRLKLAQTAV TNNTAAATVL
121  NQVLSKVAMS QPLFNQLRHP SVITGPHGHA GVPQHAAAIP STRFPSNAIA FSPPSQTRGP
181  GPSMNLPNQP PSAMVMHPFT GVMPQTPGQP AVILGIGKTG PAPATAGFYE YGKASSGQTY
241  GPETDGQPGF LPSSASTSGS VTYEGHYSHT GQDGQAAFSK DFYGPNSQGS HVASGFPAEQ
301  AGGLKSEVGP LLQGTNSQWE SPHGFSGQSK PDLTAGPMWP PPHNQPYELY DPEEPTSDRT
361  PPSFGGRLNN SKQGFIGAGR RAKEDQALLS VRPLQAHELN DFHGVAPLHL PHICSICDKK
421  VFDLKDWELH VKGKLHAQKC LVFSENAGIR CILGSAEGTL CASPNSTAVY NPAGNEDYAS
481  NLGTSYVPIP ARSFTQSSPT FPLASVGTTF AQRKGAGRVV HICNLPEGSC TENDVINLGL
541  PFGKVTNYIL MKSTNQAFLE MAYTEAAQAM VQYYQEKSAV INGEKLLIRM SKRYKELQLK
601  KPGKAVAAII QDIHSQRERD MFREADRYGP ERPRSRSPVS RSLSPRSHTP SFTSCSSSHS
661  PPGPSRADWG NGRDSWEHSP YARREEERDP APWRDNGDDK RDRMDPWAHD RKHHPRQLDK
721  AELDERPEGG RPHREKYPRS GSPNLPHSVS SYKSREDGYY RKEPKAKWDK YLKQQQDAPG
781  RSRRKDEARL RESRHPHPDD SGKEDGLGPK VTRAPEGAKA KQNEKNKTKR TDRDQEGADD
841  RKENTMAENE AGKEEQEGME ESPQSVGRQE KEAEFSDPEN TRTKKEQDWE SESEAEGESW
901  YPTNMEELVT VDEVGEEEDF IVEPDIPELE EIVPIDQKDK ICPETCLCVT TTLDLDLAQD
961  FPKEGVKAVG NGAAEISLKS PRELPSASTS CPSDMDVEMP GLNLDAERKP AESETGLSLE
1021 DSDCYEKEAK GVESSDVHPA PTVQQMSSPK PAEERARQPS PFVDDCKTRG TPEDGACEGS
1081 PLEEKASPPI ETDLQNQACQ EVLTPENSRY VEMKSLEVRS PEYTEVELKQ PLSLPSWEPE
1141 DVFSELSIPL GVEFVVPRTG FYCKLCGLFY TSEETAKMSH CRSAVHYRNL QKYLSQLAEE
1201 GLKETEGADS PRPEDSGIVP RFERKKL
```

Figure 4, continued.
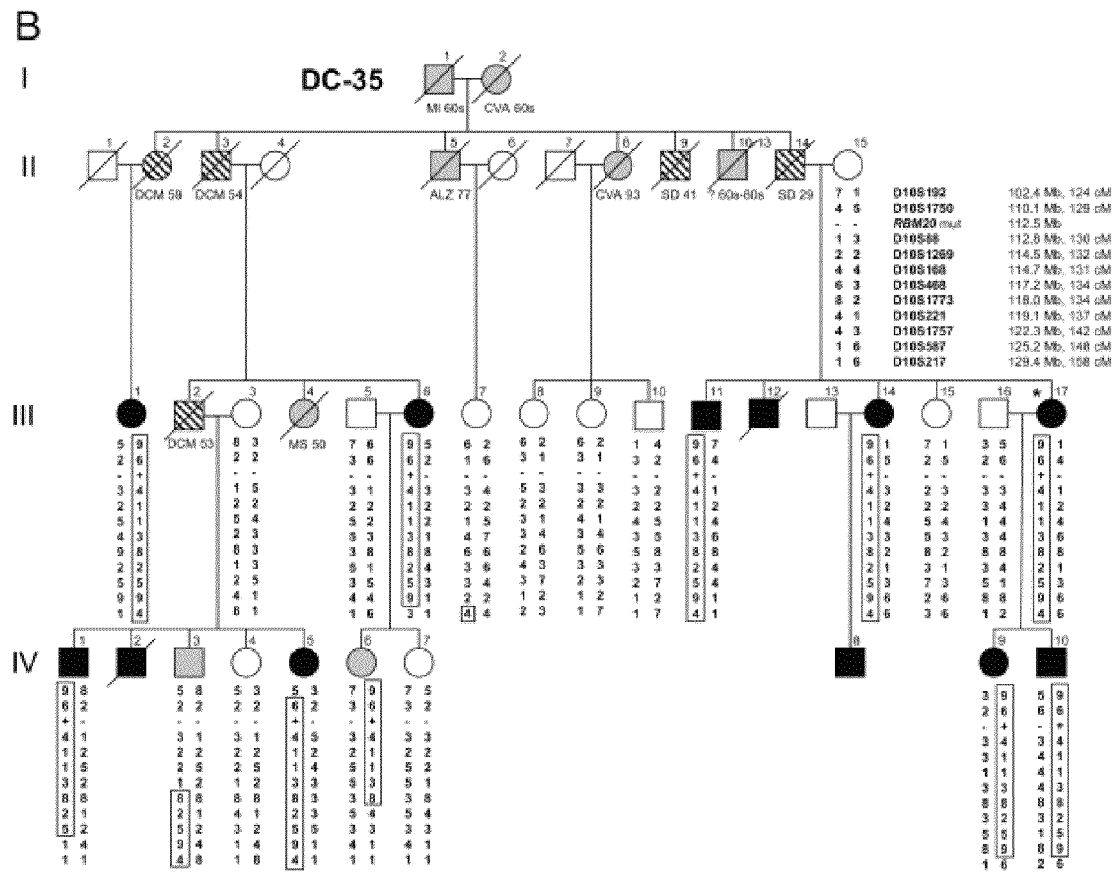

SEQUENCE LISTING

```
<160> NUMBER OF SEQ ID NOS: 75

<210> SEQ ID NO 1
<211> LENGTH: 1670
<212> TYPE: DNA
<213> ORGANISM: Homo sapiens

<400> SEQUENCE: 1
tacgtggttt tcctgtgttt gggaacttaa tgaaaaaatg cccatccttt tagaatatcg      60
gatatatgac tcagttgacc tgcttaataa ccaaacagcc ttcagagtgt atctgtatat     120
atgtgcgtat atctttgtac gtaactgttc aggctgggaa tctttatttg tttattagtc     180
tgtctgtttt tttaaaaaaa ttctgattat ttgggttttt taaagacgtg taaagccaca     240
tcttgccacc tgcaattctg cggcagagtg gagggggggt aggaagtctt gttctgaacc     300
ttacacaggt tggggtcctt gtctgggttt cagtttcttc atctcagacg tgtagatcag     360
gattctagag tatcttccaa ccctaaaatg ccttcctaat tcttttttt aacctctgag     420 cgtgccctcc ccaatagtta gcatcccttt tccatgcata aattgagctg agaaataaat     480
gagaaaactg gaggctaaga ggttggcttc attctgatac agcccaaatg taggagtggc     540
ttcaagtctt gtagctaaga ggccggctaa tggcacccag ggttaggcag ccttacccac     600
taggctggac tagggcaatc ttgcccccca gcgcccaccc cgcacacccc caggaggaga     660
gtcagaggtc cgctccctga gcatagctcc cttccaagag aaggcaagct ggaaccgagc     720
caaatcagcc cagttcttct tcctagttcc caggagcaga atgagtaaag gcacagcgag     780
tggccagtgc tgtgcttagg agaagtcctc tgcacggaag ccagaaggga ggaaaaggct     840
ttctcctgaa ccactctgtg tggttctgta gagttggag ttaagagtgt acacagttac     900
atgcacagta tatctaagac agagactgtg tgtctgtgtg tgggtggggt gggatgggag     960
gtgtgaagat tctaaatcct gctccttggc tccctcacag atatggccca gaaaggccgc    1020
ggtctcgtag tccggtgagc cggtcactct ccccgaggtc ccacactccc agcttcacct    1080
cctgcagctc ttcccacagc cctccgggcc cctcccgggc tgactgggc aatggccggg    1140 actcctggga gcactctccc tatgccagga gggaggaaga gcgagacccg gctccctgga    1200
gggacaacgg agatgacaag agggacagga tggacccctg ggcacatgat cgcaaacacc    1260
acccccggca actggacaag gctgagttgg acgagcgacc agaaggaggg aggccccacc    1320
gggagaagta cccgagatct gggtctccca acctgcccca ctctgtgtcc agctacaaaa    1380
gccgtgaaga cggctactac cggaaagagc ccaaagccaa gtgggacaag tatctgaagc    1440
agcagcagga tgcccccggg aggtccagga ggaaagacga ggccaggctg cgggaaagca    1500
gacaccccca tccggatgac tcaggcaagg aagatgggct ggggccaaag gtcactaggg    1560
cccctgaggg cgccaaggcc aagcagaatg agaaaaataa aaccaagaga actgatagag    1620
accaagaagg agctgatgat agaaaagaaa acacaatggc agagaatgag                1670
```

<210> SEQ ID NO 2
<211> LENGTH: 3684
<212> TYPE: DNA
<213> ORGANISM: Homo sapiens

<400> SEQUENCE: 2

```
atggtgctgg cagcagccat gagccaggac gcggacccca gcggtccgga gcagccggac      60
agagttgcct gcagtgtgcc tggtgcccgg gcgtccccgg caccctccgg cccgcgaggg     120
atgcagcagc cgccgccgcc gccccagcca ccgccccgc cccaagccgg cctaccccag      180
atcatccaaa atgccgccaa gctcctggac aagaacccat tctcggtcag taacccgaac     240
cctctgcttc cttcacctgc cagtctccag ctggctcaac tgcaggccca gctcaccctc     300
caccggctga agctggcaca gacagctgtc accaacaaca ctgcagccgc cacagtcctg     360
aaccaagtcc tctccaaagt ggccatgtcc agcctctct tcaatcaact gaggcatccg      420
tctgtgatca ctggccccca cggccatgct ggggttcccc aacatgctgc agccataccc     480
agtaccggt tccctctaa tgcaattgcc ttttcacccc ccagcagac acgaggcccc        540
ggaccctcca tgaaccttcc caaccagcca cccagtgcca tggtgatgca tcctttcact     600
ggggtaatgc ctcagacccc tggccagcca gcagtcatct tgggcattgg caagactggg     660
cctgctccag ctacagcagg attctatgag tatggcaaag ccagctctgg ccagacatat     720
ggccctgaaa cagatggtca gcctggcttc ctgccatcct cggcctcaac ctcgggcagt     780
gtgacctatg aagggcacta cagccacaca gggcaggatg tcaagctgc cttttccaaa     840
gatttttacg acccaactc ccaaggttca catgtggcca gcggatttcc agctgagcag     900
gctggggcc tgaaaagtga ggtcgggcca ctgctgcagg gcacaaacag ccaatgggag     960
agcccccatg gattctcggg ccaaagcaag cctgatctca cagcaggtcc catgtggcct    1020
ccaccccaca accagcccta tgagctgtac gaccccgagg aaccaacctc agacaggaca    1080
cctcctccct tcggggtcg gcttaacaac agcaaacagg ttttatcgg tgctgggcgg      1140
agggccaagg aggaccaggc gttgctatct gtgcggcccc tgcaggctca tgagctgaac    1200
gactttcacg tgtgtgcccc cctccacttg ccgcatatct gtagcatctg tgacaagaag    1260
gtgtttgatt tgaaggactg ggagctgcat gtgaaaggga gctgcacgc tcagaaatgc    1320
ctggtcttct ctgaaaatgc tggcatccgg tgtatacttg gttcggcaga gggaacattg    1380
tgtgcttctc ccaacagcac agctgtttat aaccctgctg gaatgaaga ttatgcctca     1440
aatcttggaa catcatacgt gcccattcca gcaaggtcat tcactcagtc aagccccaca    1500
tttcctttgg cttctgtggg gacaactttt gcacagcgga aggggctgg ccgtgtggtg    1560
cacatctgca atctccctga aggaagctgc actgagaatg acgtcattaa cctggggctg    1620
cccttggaa aggtcactaa ttacatcctc atgaagtcga ctaatcaggc ctttttagag     1680
atggcttaca cagaagctgc acaggccatg gtccagtatt atcaagaaaa atctgctgtg    1740
atcaatggtg agaagttgct cattcggatg tccaagagat acaaggaatt gcagctcaag    1800
aaacccggga aggccgtggc tgccatcatc aggacatcc attcccagag ggagagggac    1860
atgttccggg aagcagacag atatggccca gaaaggccgc ggtctcgtag tccggtgagc    1920
cggtcactct ccccgaggtc ccacactccc agcttcacct cctgcagctc ttcccacagc    1980
cctccgggcc cctccggc tgactgggc aatggccggg actcctggga gcactctccc    2040
tatgccagga gggaggaaga gcagacccg gctccctgga gggacaacgg agatgacaag    2100
agggacagga tggaccccctg gcacatgat cgcaaacacc accccgggca actggacaag    2160
```

```
gctgagttgg acgagcgacc agaaggaggg aggccccacc gggagaagta cccgagatct    2220
gggtctccca acctgcccca ctctgtgtcc agctacaaaa gccgtgaaga cggctactac    2280
cggaaagagc ccaaagccaa gtgggacaag tatctgaagc agcagcagga tgccccgggg    2340
aggtccagga ggaaagacga ggccaggctg cgggaaagca gacaccccca tccggatgac    2400
tcaggcaagg aagatgggct ggggccaaag gtcactaggg cccctgaggg cgccaaggcc    2460
aagcagaatg agaaaaataa aaccaagaga actgatagag accaagaagg agctgatgat    2520
agaaaagaaa acacaatggc agagaatgag gctggaaaag aggaacagga gggcatggaa    2580
gaaagccctc aatcagtggg cagacaggag aaagaagcag agttctctga tccggaaaac    2640
acaaggacaa agaaggaaca agattgggag agtgaaagtg aggcagaggg ggagagctgg    2700
tatcccacta acatggagga gctggtgaca gtggacgagg ttggggaaga agaagatttt    2760
atcgtggaac cagacatccc agagctggaa gaaattgtgc ccattgacca gaaagacaaa    2820
atttgcccag aaacatgtct gtgtgtgaca accaccttag acttagacct ggcccaggat    2880
ttccccaagg aaggagtcaa ggccgtaggg aatgggctg cagaaatcag cctcaagtca    2940
cccagagaac tgccctctgc ttccacaagc tgtcccagtg acatggacgt ggaaatgcct    3000
ggcctaaatc tggatgctga gcggaagcca gctgaaagtg agacaggcct ctccctggag    3060
gattcagatt gctacgagaa ggaggcaaag ggagtggaga gctcagatgt tcatccagcc    3120
cctacagtcc agcaaatgtc ttcccctaag ccagcagagg agagggcccg gcagccaagc    3180
ccatttgtgg atgattgcaa gaccaggggg accccgaag atggggcttg tgaaggcagc    3240
cccctggagg agaaagccag ccccccatc gaaactgacc tccaaaacca gcttgccaa    3300
gaagtgttga ccccggaaaa ctccaggtac gtggaaatga atctctgga ggtgaggtca    3360
ccagagtaca ctgaagtgga actgaaacag ccccttcctt tgccctcttg ggaaccagag    3420
gatgtgttca gtgaacttag cattcctcta ggggtggagt tcgtggttcc caggactggc    3480
ttttattgca agctgtgtgg gctgttctac acgagcgagg agacagcaaa gatgagccac    3540
tgccgcagcg ctgtccacta caggaactta cagaaatatt tgtcccagct ggccgaggag    3600
ggcctcaagg agaccgaggg ggcagatagc ccgaggccag aggacagcgg aatcgtgcca    3660
cgcttcgaaa ggaaaaagct ctga                                           3684
```

<210> SEQ ID NO 3
<211> LENGTH: 1227
<212> TYPE: PRT
<213> ORGANISM: Homo sapiens

<400> SEQUENCE: 3

```
Met Val Leu Ala Ala Ala Met Ser Gln Asp Ala Asp Pro Ser Gly Pro
1               5                   10                  15

Glu Gln Pro Asp Arg Val Ala Cys Ser Val Pro Gly Ala Arg Ala Ser
                20                  25                  30

Pro Ala Pro Ser Gly Pro Arg Gly Met Gln Gln Pro Pro Pro Pro Pro
        35                  40                  45

Gln Pro Pro Pro Pro Gln Ala Gly Leu Pro Gln Ile Ile Gln Asn
    50                  55                  60

Ala Ala Lys Leu Leu Asp Lys Asn Pro Phe Ser Val Ser Asn Pro Asn
65                  70                  75                  80

Pro Leu Leu Pro Ser Pro Ala Ser Leu Gln Leu Ala Gln Leu Gln Ala
                85                  90                  95

Gln Leu Thr Leu His Arg Leu Lys Leu Ala Gln Thr Ala Val Thr Asn
```

```
                100             105             110
Asn Thr Ala Ala Ala Thr Val Leu Asn Gln Val Leu Ser Lys Val Ala
            115             120             125
Met Ser Gln Pro Leu Phe Asn Gln Leu Arg His Pro Ser Val Ile Thr
        130             135             140
Gly Pro His Gly His Ala Gly Val Pro Gln His Ala Ala Ile Pro
145             150             155             160
Ser Thr Arg Phe Pro Ser Asn Ala Ile Ala Phe Ser Pro Pro Ser Gln
            165             170             175
Thr Arg Gly Pro Gly Pro Ser Met Asn Leu Pro Asn Gln Pro Pro Ser
        180             185             190
Ala Met Val Met His Pro Phe Thr Gly Val Met Pro Gln Thr Pro Gly
    195             200             205
Gln Pro Ala Val Ile Leu Gly Ile Gly Lys Thr Gly Pro Ala Pro Ala
    210             215             220
Thr Ala Gly Phe Tyr Glu Tyr Gly Lys Ala Ser Ser Gly Gln Thr Tyr
225             230             235             240
Gly Pro Glu Thr Asp Gly Gln Pro Gly Phe Leu Pro Ser Ser Ala Ser
            245             250             255
Thr Ser Gly Ser Val Thr Tyr Glu Gly His Tyr Ser His Thr Gly Gln
        260             265             270
Asp Gly Gln Ala Ala Phe Ser Lys Asp Phe Tyr Gly Pro Asn Ser Gln
    275             280             285
Gly Ser His Val Ala Ser Gly Phe Pro Ala Glu Gln Ala Gly Gly Leu
    290             295             300
Lys Ser Glu Val Gly Pro Leu Leu Gln Gly Thr Asn Ser Gln Trp Glu
305             310             315             320
Ser Pro His Gly Phe Ser Gly Gln Ser Lys Pro Asp Leu Thr Ala Gly
            325             330             335
Pro Met Trp Pro Pro Pro His Asn Gln Pro Tyr Glu Leu Tyr Asp Pro
        340             345             350
Glu Glu Pro Thr Ser Asp Arg Thr Pro Pro Ser Phe Gly Gly Arg Leu
    355             360             365
Asn Asn Ser Lys Gln Gly Phe Ile Gly Ala Gly Arg Arg Ala Lys Glu
    370             375             380
Asp Gln Ala Leu Leu Ser Val Arg Pro Leu Gln Ala His Glu Leu Asn
385             390             395             400
Asp Phe His Gly Val Ala Pro Leu His Leu Pro His Ile Cys Ser Ile
            405             410             415
Cys Asp Lys Lys Val Phe Asp Leu Lys Asp Trp Glu Leu His Val Lys
        420             425             430
Gly Lys Leu His Ala Gln Lys Cys Leu Val Phe Ser Glu Asn Ala Gly
    435             440             445
Ile Arg Cys Ile Leu Gly Ser Ala Glu Gly Thr Leu Cys Ala Ser Pro
    450             455             460
Asn Ser Thr Ala Val Tyr Asn Pro Ala Gly Asn Glu Asp Tyr Ala Ser
465             470             475             480
Asn Leu Gly Thr Ser Tyr Val Pro Ile Pro Ala Arg Ser Phe Thr Gln
            485             490             495
Ser Ser Pro Thr Phe Pro Leu Ala Ser Val Gly Thr Thr Phe Ala Gln
        500             505             510
Arg Lys Gly Ala Gly Arg Val Val His Ile Cys Asn Leu Pro Glu Gly
    515             520             525
```

```
Ser Cys Thr Glu Asn Asp Val Ile Asn Leu Gly Leu Pro Phe Gly Lys
        530                 535                 540

Val Thr Asn Tyr Ile Leu Met Lys Ser Thr Asn Gln Ala Phe Leu Glu
545                 550                 555                 560

Met Ala Tyr Thr Glu Ala Ala Gln Ala Met Val Gln Tyr Tyr Gln Glu
                565                 570                 575

Lys Ser Ala Val Ile Asn Gly Glu Lys Leu Leu Ile Arg Met Ser Lys
                580                 585                 590

Arg Tyr Lys Glu Leu Gln Leu Lys Lys Pro Gly Lys Ala Val Ala Ala
        595                 600                 605

Ile Ile Gln Asp Ile His Ser Gln Arg Glu Arg Asp Met Phe Arg Glu
610                 615                 620

Ala Asp Arg Tyr Gly Pro Glu Arg Pro Arg Ser Arg Ser Pro Val Ser
625                 630                 635                 640

Arg Ser Leu Ser Pro Arg Ser His Thr Pro Ser Phe Thr Ser Cys Ser
                645                 650                 655

Ser Ser His Ser Pro Pro Gly Pro Ser Arg Ala Asp Trp Gly Asn Gly
                660                 665                 670

Arg Asp Ser Trp Glu His Ser Pro Tyr Ala Arg Arg Glu Glu Glu Arg
        675                 680                 685

Asp Pro Ala Pro Trp Arg Asp Asn Gly Asp Asp Lys Arg Asp Arg Met
690                 695                 700

Asp Pro Trp Ala His Asp Arg Lys His His Pro Arg Gln Leu Asp Lys
705                 710                 715                 720

Ala Glu Leu Asp Glu Arg Pro Glu Gly Gly Arg Pro His Arg Glu Lys
                725                 730                 735

Tyr Pro Arg Ser Gly Ser Pro Asn Leu Pro His Ser Val Ser Ser Tyr
                740                 745                 750

Lys Ser Arg Glu Asp Gly Tyr Tyr Arg Lys Glu Pro Lys Ala Lys Trp
        755                 760                 765

Asp Lys Tyr Leu Lys Gln Gln Gln Asp Ala Pro Gly Arg Ser Arg Arg
770                 775                 780

Lys Asp Glu Ala Arg Leu Arg Glu Ser Arg His Pro His Pro Asp Asp
785                 790                 795                 800

Ser Gly Lys Glu Asp Gly Leu Gly Pro Lys Val Thr Arg Ala Pro Glu
                805                 810                 815

Gly Ala Lys Ala Lys Gln Asn Glu Lys Asn Lys Thr Lys Arg Thr Asp
                820                 825                 830

Arg Asp Gln Glu Gly Ala Asp Arg Lys Glu Asn Thr Met Ala Glu
        835                 840                 845

Asn Glu Ala Gly Lys Glu Gln Glu Gly Met Glu Glu Ser Pro Gln
850                 855                 860

Ser Val Gly Arg Gln Glu Lys Glu Ala Glu Phe Ser Asp Pro Glu Asn
865                 870                 875                 880

Thr Arg Thr Lys Lys Glu Gln Asp Trp Glu Ser Glu Ser Glu Ala Glu
                885                 890                 895

Gly Glu Ser Trp Tyr Pro Thr Asn Met Glu Glu Leu Val Thr Val Asp
                900                 905                 910

Glu Val Gly Glu Glu Glu Asp Phe Ile Val Glu Pro Asp Ile Pro Glu
        915                 920                 925

Leu Glu Glu Ile Val Pro Ile Asp Gln Lys Asp Lys Ile Cys Pro Glu
930                 935                 940
```

```
Thr Cys Leu Cys Val Thr Thr Leu Asp Leu Asp Leu Ala Gln Asp
945                 950                 955                 960

Phe Pro Lys Glu Gly Val Lys Ala Val Gly Asn Gly Ala Ala Glu Ile
                965                 970                 975

Ser Leu Lys Ser Pro Arg Glu Leu Pro Ser Ala Ser Thr Ser Cys Pro
                980                 985                 990

Ser Asp Met Asp Val Glu Met Pro Gly Leu Asn Leu Asp Ala Glu Arg
                995                 1000                1005

Lys Pro Ala Glu Ser Glu Thr Gly Leu Ser Leu Glu Asp Ser Asp
    1010                1015                1020

Cys Tyr Glu Lys Glu Ala Lys Gly Val Glu Ser Ser Asp Val His
    1025                1030                1035

Pro Ala Pro Thr Val Gln Gln Met Ser Ser Pro Lys Pro Ala Glu
    1040                1045                1050

Glu Arg Ala Arg Gln Pro Ser Pro Phe Val Asp Asp Cys Lys Thr
    1055                1060                1065

Arg Gly Thr Pro Glu Asp Gly Ala Cys Glu Gly Ser Pro Leu Glu
    1070                1075                1080

Glu Lys Ala Ser Pro Pro Ile Glu Thr Asp Leu Gln Asn Gln Ala
    1085                1090                1095

Cys Gln Glu Val Leu Thr Pro Glu Asn Ser Arg Tyr Val Glu Met
    1100                1105                1110

Lys Ser Leu Glu Val Arg Ser Pro Glu Tyr Thr Glu Val Glu Leu
    1115                1120                1125

Lys Gln Pro Leu Ser Leu Pro Ser Trp Glu Pro Glu Asp Val Phe
    1130                1135                1140

Ser Glu Leu Ser Ile Pro Leu Gly Val Glu Phe Val Val Pro Arg
    1145                1150                1155

Thr Gly Phe Tyr Cys Lys Leu Cys Gly Leu Phe Tyr Thr Ser Glu
    1160                1165                1170

Glu Thr Ala Lys Met Ser His Cys Arg Ser Ala Val His Tyr Arg
    1175                1180                1185

Asn Leu Gln Lys Tyr Leu Ser Gln Leu Ala Glu Glu Gly Leu Lys
    1190                1195                1200

Glu Thr Glu Gly Ala Asp Ser Pro Arg Pro Glu Asp Ser Gly Ile
    1205                1210                1215

Val Pro Arg Phe Glu Arg Lys Lys Leu
    1220                1225

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggaaggaca agggactg                                                   19

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
aacagccaga aggacaccga ct                                              22

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccagctgtgc atctagacc                                                  19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctttgccat actcatagaa t                                               21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tacccggttt ccctctaatg                                                 20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gttcctcggg gtcgtacag                                                  19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccaactccc aaggttcac                                                  19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```
ctcccagcct gtcttggac                                                19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccctgcctg accagtgtc                                                19

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgtcctcct gaacagcact ta                                            22

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccggtttccc tttctcg                                                  17

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctttctaca tccgtgaga                                                19

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagaggtaca atcatgccaa tc                                            22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
cttgggacca ggagttagtt ca                                          22
```

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
gtttagggga aagatagcca tta                                         23
```

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
atcaccagca aaaacaccta cgc                                         23
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
atgccttgtg ctgaatcttg                                             20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
aacacggagg agaaactcat                                             20
```

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
ccccacccag ttcagcatta ta                                          22
```

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
agaacagggc acagcatgac tc                                          22
```

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agagttggga gttaagagtg ta                                              22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctgctgctt cagatacttg t                                               21

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aactggacaa ggctgagttg gac                                             23

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggggaagaa attgatcatt ac                                              22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agagctggga cctgcattca ata                                             23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgtgggtaa agatcgcttc a                                               21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgatttgagt ggtccttatg gc                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccaggcattt ccacgtccat gt                                              22

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agaaattgtg cccattgac                                                  19

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgaggaaagg ggagatagtt ac                                              22

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgccttggtt catgtttt                                                   18

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caaaatgcca aaagctctc                                                  20

```
<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcagtaacca gccaaggtca ac                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agagcagcct gatggaatca ag                                              22

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gattgaggca tgtccg                                                     16

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acacctgggt gacttgct                                                   18

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cctaccccag atcatccaaa atgc                                            24

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aacaaacact ttgcagtcag ttataca                                         27

<210> SEQ ID NO 42
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gaacccattc tcggtcagta accc                                              24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tctctctgcc cttcctccat tagt                                              24

<210> SEQ ID NO 44
<211> LENGTH: 52
<212> TYPE: DNA
<213> ORGANISM: Homo sapiens

<400> SEQUENCE: 44
gtccaagaca ggctgggagc cacagcyaga agcctgggca ggcctttccc ca               52

<210> SEQ ID NO 45
<211> LENGTH: 52
<212> TYPE: DNA
<213> ORGANISM: Homo sapiens

<400> SEQUENCE: 45
ccaagacagg ctgggagcca cagctaraag cctgggcagg cctttcccca tg               52

<210> SEQ ID NO 46
<211> LENGTH: 59
<212> TYPE: DNA
<213> ORGANISM: Homo sapiens
<220> FEATURE:
<221> NAME/KEY: modified_base
<222> LOCATION: (27)..(34)
<223> OTHER INFORMATION: This region may or may not be present

<400> SEQUENCE: 46
tttctctatc ttcctctatc tgtctatcta tctatctatc tatctatcta tctatctat        59

<210> SEQ ID NO 47
<211> LENGTH: 52
<212> TYPE: DNA
<213> ORGANISM: Homo sapiens

<400> SEQUENCE: 47
acaggtgagg ccccaagccc caagtcycca ggcaggttct gggcagtggg aa               52

<210> SEQ ID NO 48
<211> LENGTH: 52
<212> TYPE: DNA
<213> ORGANISM: Homo sapiens

<400> SEQUENCE: 48
aggacagcgg aatcgtgcca cgcttcsaaa ggaaaaagct ctgatgcttc tg               52
```

```
<210> SEQ ID NO 49
<211> LENGTH: 52
<212> TYPE: DNA
<213> ORGANISM: Homo sapiens

<400> SEQUENCE: 49
tgctgttcag gaggacaggc tcatgcrtag gctcaacaca tattcactga gc          52

<210> SEQ ID NO 50
<211> LENGTH: 52
<212> TYPE: DNA
<213> ORGANISM: Homo sapiens

<400> SEQUENCE: 50
aggagcttgt gcttcacagg ggccagrgag atgataaaca aaatgaacaa ga          52

<210> SEQ ID NO 51
<211> LENGTH: 52
<212> TYPE: DNA
<213> ORGANISM: Homo sapiens

<400> SEQUENCE: 51
tcacatgcta attctttgtt taacttmtta aggagccggt ttccctttct cg          52

<210> SEQ ID NO 52
<211> LENGTH: 52
<212> TYPE: DNA
<213> ORGANISM: Homo sapiens

<400> SEQUENCE: 52
ggcttctgtg gggacaactg tgagtaygga aacattttct ctagaaatta at          52

<210> SEQ ID NO 53
<211> LENGTH: 59
<212> TYPE: DNA
<213> ORGANISM: Homo sapiens
<220> FEATURE:
<221> NAME/KEY: modified_base
<222> LOCATION: (27)..(34)
<223> OTHER INFORMATION: This region may or may not be present

<400> SEQUENCE: 53
tttctctatc ttcctctatc tgtctatcta tctatctatc tatctatcta tctatctat     59

<210> SEQ ID NO 54
<211> LENGTH: 52
<212> TYPE: DNA
<213> ORGANISM: Homo sapiens

<400> SEQUENCE: 54
gccattctta acataaagag gcgatgycgt agctggcctt ctgttggcat gg          52

<210> SEQ ID NO 55
<211> LENGTH: 52
<212> TYPE: DNA
<213> ORGANISM: Homo sapiens

<400> SEQUENCE: 55
atccccacct gagagagaag ctcaatrcta actcctgtca ccgttgatta gt          52

<210> SEQ ID NO 56
<211> LENGTH: 52
<212> TYPE: DNA
<213> ORGANISM: Homo sapiens
```

<400> SEQUENCE: 56
acaggtgagg ccccaagccc caagtcycca ggcaggttct gggcagtggg aa        52

<210> SEQ ID NO 57
<211> LENGTH: 11
<212> TYPE: DNA
<213> ORGANISM: Homo sapiens

<400> SEQUENCE: 57
gccgcrgtct c        11

<210> SEQ ID NO 58
<211> LENGTH: 11
<212> TYPE: DNA
<213> ORGANISM: Homo sapiens

<400> SEQUENCE: 58
ggtctmgtag t        11

<210> SEQ ID NO 59
<211> LENGTH: 12
<212> TYPE: DNA
<213> ORGANISM: Homo sapiens

<400> SEQUENCE: 59
ggtctcrtag tc        12

<210> SEQ ID NO 60
<211> LENGTH: 11
<212> TYPE: DNA
<213> ORGANISM: Homo sapiens

<400> SEQUENCE: 60
ctcgtrgtcc g        11

<210> SEQ ID NO 61
<211> LENGTH: 11
<212> TYPE: DNA
<213> ORGANISM: Homo sapiens

<400> SEQUENCE: 61
tagtcyggtg a        11

<210> SEQ ID NO 62
<211> LENGTH: 28
<212> TYPE: PRT
<213> ORGANISM: Homo sapiens

<400> SEQUENCE: 62

Tyr Gly Pro Glu Arg Pro Arg Ser Arg Ser Pro Val Ser Arg Ser Leu
1               5                   10                  15

Ser Pro Arg Ser His Thr Pro Ser Phe Thr Ser Cys
            20                  25

<210> SEQ ID NO 63
<211> LENGTH: 28
<212> TYPE: PRT
<213> ORGANISM: Pan troglodytes

<400> SEQUENCE: 63

Tyr Gly Pro Glu Arg Pro Arg Ser Arg Ser Pro Val Ser Arg Ser Leu
1               5                   10                  15

Ser Pro Arg Ser His Thr Pro Ser Phe Thr Ser Cys
            20                  25

<210> SEQ ID NO 64
<211> LENGTH: 28
<212> TYPE: PRT
<213> ORGANISM: Canis familiaris

<400> SEQUENCE: 64

Tyr Gly Pro Glu Arg Pro Arg Ser Arg Ser Pro Val Ser Arg Ser Leu
1               5                   10                  15

Ser Pro Arg Ser His Thr Pro Ser Phe Thr Ser Cys
            20                  25

<210> SEQ ID NO 65
<211> LENGTH: 28
<212> TYPE: PRT
<213> ORGANISM: Bos taurus

<400> SEQUENCE: 65

Tyr Ala Pro Glu Arg Pro Arg Ser Arg Ser Pro Val Ser Arg Ser Leu
1               5                   10                  15

Ser Pro Arg Ser His Thr Pro Ser Phe Thr Ser Cys
            20                  25

<210> SEQ ID NO 66
<211> LENGTH: 19
<212> TYPE: PRT
<213> ORGANISM: Mus musculus

<400> SEQUENCE: 66

Tyr Gly Pro Glu Arg Pro Arg Ser Arg Ser Pro Met Ser Arg Ser Leu
1               5                   10                  15

Ser Pro Arg

<210> SEQ ID NO 67
<211> LENGTH: 19
<212> TYPE: PRT
<213> ORGANISM: Rattus norvegicus

<400> SEQUENCE: 67

Tyr Gly Pro Glu Arg Pro Arg Ser Arg Ser Pro Met Ser Arg Ser Leu
1               5                   10                  15

Ser Pro Arg

<210> SEQ ID NO 68
<211> LENGTH: 28
<212> TYPE: PRT
<213> ORGANISM: Gallus gallus

<400> SEQUENCE: 68

Tyr Gly Thr Glu Arg Pro Arg Ser Arg Ser Pro Ile Ser Arg Ser Leu
1               5                   10                  15

Ser Pro Arg Ser His Thr Pro Ser Phe Thr Ser Cys
            20                  25

<210> SEQ ID NO 69
<211> LENGTH: 28
<212> TYPE: PRT
<213> ORGANISM: Danio rerio

<400> SEQUENCE: 69

```
Tyr Leu Pro Glu Arg Pro Arg Ser Arg Ser Pro Ile Ser Arg Ser Leu
1               5                   10                  15

Ser Pro Arg Ser His Ser Pro Ser Phe Thr Ser Cys
            20                  25
```

<210> SEQ ID NO 70
<211> LENGTH: 26
<212> TYPE: PRT
<213> ORGANISM: Tetraodon nigroviridis

<400> SEQUENCE: 70

```
Tyr Leu Pro Glu Arg Thr Arg Ser Arg Ser Pro Val Ser Arg Ser Leu
1               5                   10                  15

Ser Pro Arg Ser Pro Ser Phe Thr Ser Cys
            20                  25
```

<210> SEQ ID NO 71
<211> LENGTH: 12
<212> TYPE: DNA
<213> ORGANISM: Homo sapiens

<400> SEQUENCE: 71
gccgcggtct ca                                                        12

<210> SEQ ID NO 72
<211> LENGTH: 12
<212> TYPE: DNA
<213> ORGANISM: Homo sapiens

<400> SEQUENCE: 72
ggtctcgtag ta                                                        12

<210> SEQ ID NO 73
<211> LENGTH: 13
<212> TYPE: DNA
<213> ORGANISM: Homo sapiens

<400> SEQUENCE: 73
ggtctcgtag tca                                                       13

<210> SEQ ID NO 74
<211> LENGTH: 12
<212> TYPE: DNA
<213> ORGANISM: Homo sapiens

<400> SEQUENCE: 74
ctcgtagtcc gg                                                        12

<210> SEQ ID NO 75
<211> LENGTH: 12
<212> TYPE: DNA
<213> ORGANISM: Homo sapiens

<400> SEQUENCE: 75
tagtccggtg at                                                        12

RIBONUCLEIC ACID BINDING MOTIF PROTEIN 20 SEQUENCE VARIANTS

CROSS-REFERENCE TO RELATED APPLICATIONS

This application is a continuation of U.S. application Ser. No. 13/105,669, filed May 11, 2011, which claims the benefit of U.S. Provisional Application Ser. No. 61/334,022, filed May 12, 2010. The disclosures of the prior applications are considered part of (and are incorporated by reference in) the disclosure of this application.

STATEMENT AS TO FEDERALLY SPONSORED RESEARCH

This invention was made with government support under HL071225 awarded by National Institutes of Health. The government has certain rights in the invention.

BACKGROUND

1. Technical Field

This document relates to methods and materials for using nucleic acid and amino acid sequence variants of ribonucleic acid binding motif protein 20 (RBM20). For example, this document relates to methods and materials for using nucleic acid sequence variants and/or their corresponding amino acid variants of RBM20 that are associated with dilated cardiomyopathy to identify mammals (e.g., humans) at risk of having dilated cardiomyopathy that is likely to progress to heart failure.

2. Background Information

Dilated cardiomyopathy (DCM) is a disease of the heart muscle characterized by cardiac enlargement and impaired systolic function of the heart. The more dilated the heart becomes, the less it is able to contract and pump blood from the left ventricle into the aorta. Inefficient blood pumping can lead to ankle and abdominal swelling, fatigue, shortness of breath, palpitations, and irregular heartbeat. A collection of all or a few of these symptoms is indicative of heart failure. The primary manifestation of DCM is heart failure, a major public health concern with an estimated 5.7 Americans living with heart failure and 670,000 new diagnoses each year, according to the American Heart Association. Onset of heart failure symptoms in DCM typically portends advanced myocardial disease and risk for sudden death (Desai et al., *JAMA*, 292:2874-9 (2006)) after years of asymptomatic progression of heart muscle weakening.

In the majority of cases of DCM, the cause is unknown, and the condition is called idiopathic DCM. Idiopathic DCM is hereditary in at least 20% of cases (Michels et al., *N Eng. J. Med.*, 326:77-82 (1992)), suggesting genetic factors are important in its pathogenesis yet the basic mechanisms behind the pathogenicity of DCM remain largely unsolved. Familial cases of DCM provide an opportunity to discover unsuspected molecular bases, which could enable pre-clinical risk detection. In recent years, mutations in genes encoding contractile, cytoskeletal, nuclear membrane, calcium-regulating, and ion channel polypeptides have been associated with familial and sporadic DCM. Although these reports clearly establish DCM as a genetically heterogeneous disorder, the alterations in the molecular and cellular mechanisms leading to DCM as a result of these mutations remain poorly delineated.

SUMMARY

This document provides methods and materials for using nucleic acid and/or amino acid sequence variants of RBM20. For example, this document provides methods and materials for using nucleic acid sequence variants and/or their corresponding amino acid variants of RBM20 that are associated with dilated cardiomyopathy to identify mammals (e.g., humans) at risk of having dilated cardiomyopathy that is likely to progress to heart failure. As described herein, a mutation hotspot within a highly conserved arginine/serine (RS)-rich domain of RBM20 is associated with DCM. The presence or absence of RBM20 sequence variants in an individual can be used to determine whether or not the individual is at risk of having DCM that is likely to progress to heart failure.

In general, one aspect of this document features a method for assessing a human for the presence of or an increased risk of developing dilated cardiomyopathy. The method comprises, or consists essentially of, determining whether or not the human contains a mutation in a nucleic acid encoding RBM20, classifying the human as having or as being at an increased risk of developing said dilated cardiomyopathy if the mutation is present, and classifying the human as not having or s not being at an increased risk of developing the dilated cardiomyopathy if the mutation is absent. The method can comprise determining the presence of a mutation corresponding to a nucleotide change of RBM20 at position 1901, 1906, 1907, 1909, or 1913. The method can comprise recording an echocardiogram or performing electrocardiography on the human. These mutations may be determined using in situ hybridization and/or a nucleic acid detection assay.

In another aspect, this document features a method for assessing a human for the presence of or an increased risk of developing dilated cardiomyopathy. The method comprises, or consists essentially of, determining whether or not the human contains a mutation in the amino acid sequence of a RBM20, wherein the mutation is associated with dilated cardiomyopathy, classifying the human as having or as being at an increased risk of developing dilated cardiomyopathy if the mutation is present, and classifying the human as not having or as not being at an increased risk of developing dilated cardiomyopathy if the mutation is absent. The method can comprise determining whether the mutation is within the arginine/serine-rich domain of RBM20. In some cases, the mutation can correspond to an amino acid change of RBM20 at position 634, 636, 637, or 638. The method can comprise recording an echocardiogram or performing electrocardiography on the human.

In some cases, the human can be a human having a family history of cardiomyopathy, heart failure, or sudden death at an early age. The family history can be identified by analyzing a family tree. In other cases, the human can be a human having a relative with cardiomyopathy or heart failure.

In another aspect, this document features an antibody that binds to an RBM20 variant polypeptide that is different than the wild type RBM20 polypeptide. In some cases, the antibody can lack the ability to bind to wild type RBM20.

In another aspect, this document features a kit comprising, or consisting essentially of, a pair of primers designed to amplify position 1901, 1906, 1907, 1909, or 1913 of RBM20 or a probe configured to detect a sequence variant at position 1901, 1906, 1907, 1909, or 1913 or RBM20.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are

DESCRIPTION OF DRAWINGS

FIG. 1 is a nucleotide sequence (SEQ ID NO:1) that is a portion of the RBM20 gene sequence (nucleotides 112571036-112573705) of GenBank® Accession No. NC_000010.10 (GI No. 224589801). Exon 9 encoding the RS domain is indicated in bold text. The positions of the substitutions leading to the RBM20 Pro638Leu, Arg634Glu, Arg636Ser, Arg636His, and Ser637Gly mutations are underlined.

FIG. 2 is a nucleotide sequence that is the RBM20 coding sequence (nucleotides 59-3742 of GenBank® Accession No. NM_00134363.1 (GI No. 197276593; SEQ ID NO:2). The positions of the substitutions leading to the RBM20 Pro638Leu, Arg634Glu, Arg636Ser, Arg636His, and Ser637Gly mutations are underlined and bold.

FIG. 3 is the RBM20 amino acid sequence (GenBank® Accession No. NP_001127835.1 (GI No. 197276594; SEQ ID NO:3). The position of the RBM20 Pro638Leu, Arg634Glu, Arg636Ser, Arg636His, and Ser637Gly mutations are underlined and bold.

DETAILED DESCRIPTION

Figure 4:
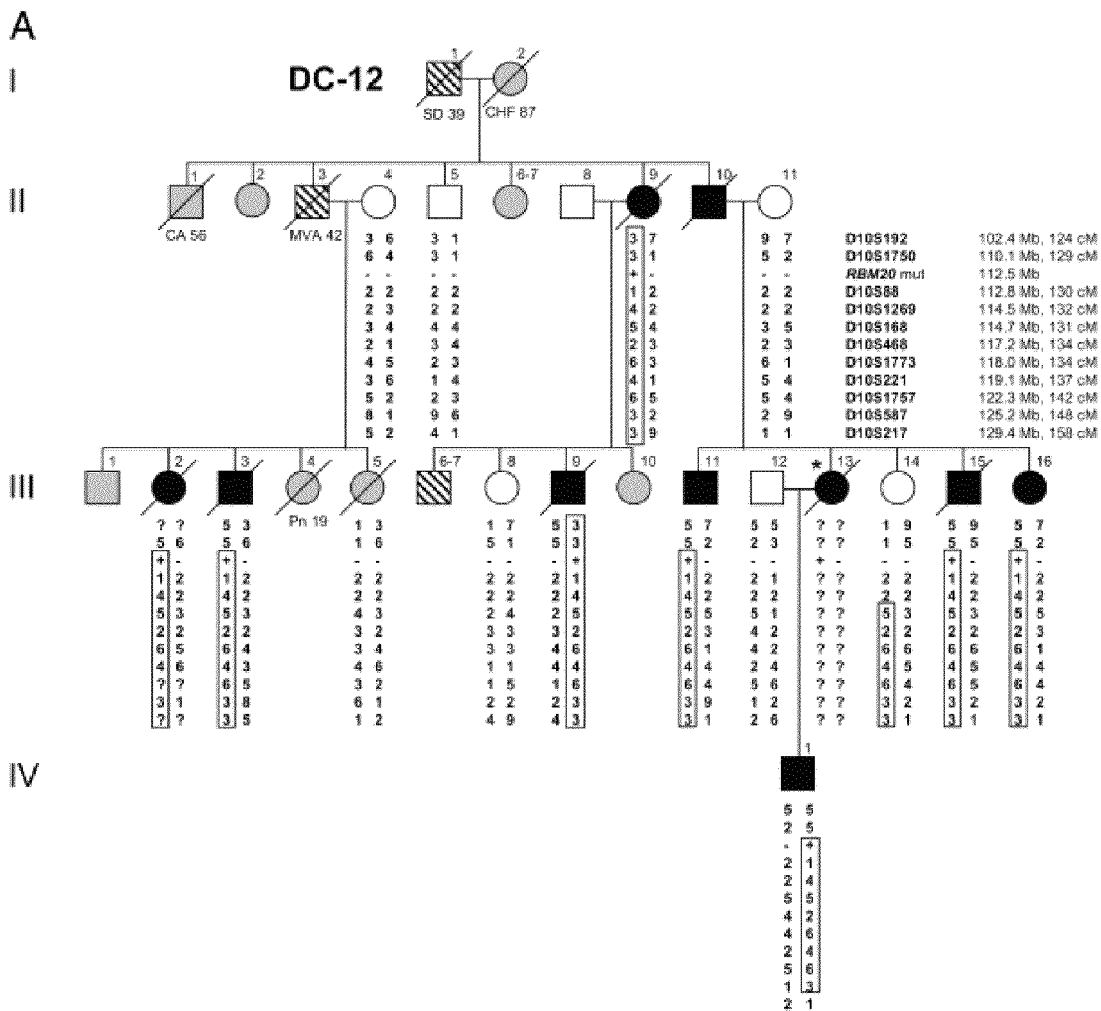
FIG. 4 is a pedigree structure for index families with hereditary DCM for (A) DC-12, a family with Scottish ancestry, and (B) DC-35, a family with Norwegian ancestry. Haplotypes for markers in the 10q25.2 chromosomal region, the location of RBM20, are shown in columns beneath family members who underwent genetic evaluation. Square=male; circle=female; solid=affected; open=unaffected; gray=clinical status unknown; parallel diagonal lines=suspected dilated cardiomyopathy (DCM) on the basis of family history; slash through the symbol=deceased, with cause of/age at death indicated. Question marks indicate genotypes that could not be scored from paraffin-embedded samples. The RBM20 missense mutations (RBM20 mut), which cosegregate with DCM, are indicated by plus symbols; minus symbols indicate wild-type sequence. An asterisk represents the proband (first affected family member who sought medical attention for DCM symptoms). ALZ=Alzheimer's disease; CA=cancer; CHF=congestive heart failure; CVA=cerebrovascular accident; MI=myocardial infarction; MS=multiple sclerosis; MVA=motor vehicle accident; Pn=pneumonia; SD=sudden death; Tx=cardiac transplantation.

This document provides RBM20 nucleic acid and amino acid sequence variants. Located on the human chromosome 10q25, the RBM20 gene contains 14 exons and encodes a protein of 1227 amino acid residues. The RBM20 protein comprises numerous domains, including a ribonucleic acid recognition motif 1 (RRM-1), an arginine/serine (RS)-rich region, and a U1 zinc finger (zf-U1). The RS domain is a highly conserved functional domain that is known to interact directly with intronic sequences in the pre-messenger ribonucleic acid (mRNA) and mediate protein-protein interactions within the spliceosome, a large multiprotein complex that orchestrates constitutive and alternative splicing of pre-mRNA. The specific function of RBM20 in the human heart and how the downstream effects of RBM20 sequence variants cause DCM has yet to be elucidated, but detection of such RBM20 sequence variants can identify individuals likely to develop clinically aggressive DCM.

Nucleic Acid Molecules

Provided herein are isolated nucleic acids that include an RBM20 nucleic acid sequence. The RBM20 nucleic acid sequences include a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-RBM20 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids provided herein are at least about 8 nucleotides in length. For example, the nucleic acid can be at least about 8, 9, 10-20 (e.g., 11, 12, 13, 14, 15, 16, 17, 18, 19, or 20 nucleotides in length), 10-50, 15-50, 20-50, 20-75, 50-100, or greater than 100 nucleotides in length (e.g., greater than 150, 200, 250, 300, 350, 400, 450, 500, 750, or 1000 nucleotides in length). Nucleic acids can be in a sense or antisense orientation, can be complementary to the RBM20 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.*, 7:187-195; and Hyrup et al. (1996) *Bioorgan. Med. Chem.*, 4:5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in an RBM20 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference RBM20 nucleic acid sequence is provided in GenBank® (Accession No. NC_000010.10; GI No. 224589801); a portion of this sequence is provided in FIG. 1 and SEQ ID NO:1. The reference RBM20 coding sequence is provided in GenBank® (CCDS44477.1) and FIG. 2 and SEQ ID NO:2, and the corresponding reference RBM20 amino acid sequence is provided in GenBank® (NP_001127835.1; GI No. 197276594) and FIG. 3 and SEQ ID NO:3. The mRNA reference sequence also is found in GenBank® (Accession No. NM_001134363.1; GI No. 197276593). The nucleic acid and amino acid reference sequences also are referred to herein as "wild type."

In some embodiments, an RBM20 nucleotide sequence variant encodes an RBM20 polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-250, 250-500, 500-1000, 1000-1500, 1500-2500 residues, or a full-length RBM20 polypeptide). RBM20 polypeptides may or may not have the ability to bind pre-mRNA or proteins, or may have altered binding strengths relative to the reference RBM20 polypeptide. Polypeptides that do not have high binding affinity or have altered binding affinity can be useful for diagnostic purposes (e.g., for producing antibodies having specific binding affinity for variant RBM20 polypeptides).

Corresponding RBM20 polypeptides, irrespective of length, that differ in amino acid sequence are herein referred to as variants. For example, an RBM20 nucleic acid sequence that includes an adenine at position 1901 relative to the adenine in the translation initiation codon, position 1901 of SEQ ID NO:2, (c.1901 G>A) encodes a RBM20 polypeptide having a glutamine at amino acid residue 634. This polypeptide (Arg634Gln) would be considered a variant with respect to the reference RBM20 polypeptide that contains an arginine at amino acid residue 634. Additional non-limiting examples of RBM20 sequence variants that alter amino acid sequence include variants at nucleotides 1906, 1907, 1909, and 1913 relative to the adenine in the translation initiation codon (positions 1906, 1907, 1909, and 1913, respectively, of SEQ ID NO:2). For example, an RBM20 nucleic acid molecule can include an adenine at nucleotide 1906 (c.1906 C>A) and encode an RBM20 polypeptide having a serine at amino acid residue 636 in place of an arginine residue (Arg636Ser); or an adenine at nucleotide 1907 (c.1907 G>A) and encode an RBM20 polypeptide having a histidine at amino acid residue 636 in place of an arginine residue (Arg636His); or a guanine at nucleotide 1909 (c.1909 A>G) and encode an RBM20 polypeptide having a glycine at amino acid residue 637 in place of a serine residue (Ser637Gly); or a thymine at nucleotide 1913 (c.1913 C>T) and encode an RBM20 polypeptide having a leucine amino acid residue 638 in place of a proline residue (Pro638Leu).

RBM20 variants as described above are encoded by a series of RBM20 alleles. These alleles represent nucleic acid sequences containing sequence variants typically multiple sequence variants, within coding and non-coding sequences. Representative examples of single nucleotide variants are described herein. The potential complexity of RBM20 binding characteristics emphasizes a need for determining single nucleotide variants (i.e., single nucleotide polymorphisms, SNPs) as well as complete RBM20 haplotypes (i.e., the set of alleles on one chromosome or a part of a chromosome) of patients.

In some embodiments, a RBM20 nucleic acid molecule can consist essentially of at least ten (e.g., at least 12, at least 15, at least 18, at least 20, or at least 25) contiguous nucleotides of a RBM20 reference sequence (e.g., SEQ ID NO:1 or SEQ ID NO:2). Such nucleic acids can contain an adenine substitution at the position corresponding to nucleotide 1901 of SEQ ID NO:2; or an adenine substitution at the position corresponding to nucleotide 1906 of SEQ ID NO:2; or an adenine substitution at the position corresponding to nucleotide 1907 of SEQ ID NO:2; or a guanine substitution at the position corresponding to nucleotide 1909 of SEQ ID NO:2; or an adenine substitution at the position corresponding to nucleotide 1913 of SEQ ID NO:2. An RBM20 nucleic acid "consisting essentially of" a particular sequence has the basic and novel characteristic that it can be used to distinguish, based upon hybridization, a nucleic acid having a sequence that contains a variant from a corresponding nucleic acid having a sequence that does not contain the variant (e.g., a wild type sequence). Such nucleic acid molecules can include additional sequences or labels (e.g., a tag or a fluorescent label as disclosed herein), provided that such additions do not affect the basic and novel characteristic of the nucleic acid molecules.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing an RBM20 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, the reference sequences depicted in FIG. 1 or 2 can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified include those described herein.

RBM20 Polypeptides

Isolated RBM20 polypeptides provided herein include an amino acid sequence variant relative to the reference RBM20 (SEQ ID NO:3; GenBank® Accession No. NP_001127835.1). The term "isolated" as used with respect to an RBM20 polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

RBM20 polypeptides can include sequence variants at amino acid residues 634, 636, 637, or 638. In particular, a glutamine residue can be substituted at position 634, a serine or histidine residue can be substituted at position 636, a glycine residue can be substituted at position 637, a leucine can be substituted at position 639, or any combination thereof. In some embodiments, binding characteristics of RBM20 polypeptides to either pre-mRNA or other proteins is altered relative to the reference RBM20. Certain RBM20 mutants can have reduced binding affinities, while other mutants can have binding affinities that are comparable to the reference RBM20. Other mutants can have increased binding affinities relative to the reference RBM20. Binding affinities of RBM20 polypeptides can be assessed in vitro. For example, surface plasmon resonance may be used for studying real-time biomolecular interactions.

In bacterial systems, a strain of *Escherichia coli* can be used to express RBM20 mutant polypeptides. For example, BL-21 cells can be transformed with a pGEX vector containing an RBM20 nucleic acid sequence. The transformed bacteria can be grown exponentially and then stimulated with isopropylthiogalactopyranoside (IPTG) prior to harvesting. RBM20-GST fusion proteins produced from the pGEX expression vector can be purified from lysed cells by adsorption to glutathione-agarose beads followed by elution in the presence of free glutathione. The pGEX vectors are designed to include thrombin or factor Xa protease cleavage sites so that the expressed RBM20 polypeptide can be released from the GST moiety.

In eukaryotic host cells, a number of viral-based expression systems can be utilized to express RBM20 variant polypeptides. A nucleic acid encoding a polypeptide can be cloned into, for example, a baculoviral vector such as pBlue-Bac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides can be identified by standard methodology. Alternatively, a nucleic acid encoding a polypeptide can be introduced into a SV40, retroviral, or vaccinia based viral vector and used to infect suitable host cells.

Eukaryotic cell lines that stably express RBM20 variant polypeptides can be produced using expression vectors with the appropriate control elements and a selectable marker. For example, the eukaryotic expression vector pCR3.1 (Invitrogen, San Diego, Calif.) and p91023(B) (see Wong et al. (1985) *Science* 228:810-815) or modified derivatives thereof are suitable for expression of RBM20 variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, for example, by antibiotic resistance to G418, kanamycin, or hygromycin. Alternatively, amplified sequences can be ligated into a eukaryotic expression vector such as pCR3.1, pcDNA3.1 (Invitrogen), or pcDNA4/HisMax TOPO (Promega) and then transcribed and translated in vitro using wheat germ extract or rabbit reticulocyte lysate.

RBM20 variant polypeptides can be purified by known chromatographic methods including ion exchange and gel filtration chromatography. RBM20 polypeptides can be "engineered" to contain a tag sequence described herein that allows the polypeptide to be purified (e.g., captured onto an affinity matrix). Immunoaffinity chromatography also can be used to purify RBM20 polypeptides.

Detecting RBM20 Sequence Variants

RBM20 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al. (1995) Nat. Biotechnol. 15:33-39), denaturing high performance liquid chromatography (DHPLC, Underhill et al. (1997) Genome Res. 7:996-1005), infrared matrix-assisted laser desorption/ionization (IR-MALDI) mass spectrometry (WO 99/57318), and combinations of such methods. Other useful detection techniques include, but are not limited to fluorescence in situ hybridization (FISH), direct DNA sequencing, PFGE analysis, Southern blot analysis, RNase protection assay, allele-specific oligonucleotide (ASO), dot blot analysis, or DNA microchip technology.

Genomic DNA generally is used in the analysis of RBM20 nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the RBM20 gene can be amplified then directly sequenced. Dye primer sequencing can be used to increase the accuracy of detecting heterozygous samples.

Nucleic acid molecules provided herein can be used to detect variant RBM20 sequences. For example, allele specific hybridization also can be used to detect sequence variants, including complete haplotypes of a mammal (e.g., a human). See, Stoneking et al. (1991) Am. J. Hum. Genet. 48:370-382; and Prince et al. (2001) Genome Res. 11:152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C.

Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For RBM20 sequence variants that do not alter a common restriction site, mutagenic primers can be designed that introduce a restriction site when the variant allele is present or when the wild type allele is present. A portion of RBM20 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of RBM20 nucleic acid can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al. (2001) Genome Res. 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, RBM20 variants can be detected by antibodies that have specific binding affinity for variant RBM20 polypeptides. Variant RBM20 polypeptides can be produced in various ways, including recombinantly, as discussed above. Host animals such as rabbits, chickens, mice, guinea pigs, and rats can be immunized by injection of an RBM20 variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using an RBM20 variant polypeptide and standard hybridoma technology. In particular, monoclonal antibodies can be obtained by any technique that provides for the production of antibody molecules by continuous cell lines in culture such as described by Kohler et al. (1975) *Nature* 256:495, the human B-cell hybridoma technique (Kosbor et al. (1983) *Immunology Today* 4:72; Cote et al. (1983) *Proc. Natl. Acad. Sci. USA* 80:2026), and the EBV-hybridoma technique (Cole et al., *Monoclonal Antibodies and Cancer Therapy*, Alan R. Liss, Inc., pp. 77-96 (1983). Such antibodies can be of any immunoglobulin class including IgG, IgM, IgE, IgA, IgD and any subclass thereof. A hybridoma producing monoclonal antibodies can be cultivated in vitro or in vivo.

Antibody fragments that have specific binding affinity for an RBM20 variant polypeptide can be generated using known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science*, 246:1275 (1989). Once produced, antibodies or fragments thereof are tested for recognition of RBM20 variant polypeptides by standard immunoassay methods including ELISA techniques, radioimmunoassays and Western blotting. See, *Short Protocols in Molecular Biology*, Chapter 11, Green Publishing Associates and John Wiley & Sons, edited by Ausubel et al., 1992.

Methods

This document provides methods that can be used to determine whether a mammal (e.g., a human) is at risk for dilated cardiomyopathy (DCM). For example a method of screening RBM20 can include determining whether the mammal has an adenine substitution at the position corresponding to nucleotide 1901 of SEQ ID NO:2, an adenine substitution at the position corresponding to nucleotide 1906 of SEQ ID NO:2, an adenine substitution at the position corresponding to nucleotide 1907 of SEQ ID NO:2, a guanine substitution at the position corresponding to nucleotide 1909 of SEQ ID NO:2, or a thymine substitution at the position corresponding to nucleotide 1913 of SEQ ID NO:2. If the RBM20 nucleotide sequence variant is present, the mammal has or is at risk for RBM20-related DCM and heart failure.

The methods provided herein can be used to predict whether a mammal (e.g., a human) will develop DCM and heart failure, based on the presence or absence of an RBM20 mutation. In some cases, a human may have a family history of DCM or sudden death related to cardiac problem. Family history or relatives with DCM or cardiac problems can be identified by examining medical records or family tree history. The methods can also be used to identify the underlying cause of familial DCM. The methods can also be used to identify relatives of affected mammals likely to develop DCM and heart failure. Thus, these methods can facilitate decisions regarding the course of evaluation and treatment in humans with and without RBM20 mutations. For example, if an RBM20 sequence variant is detected, follow-up echocardiograms could be scheduled on an annual basis to monitor and detect dilation and/or reduced contractility of the heart before the development of symptomatic, advanced DCM. Early detection would enable early initiation of medications like beta-adrenergic receptor blockers and angiotensin-converting enzyme inhibitors proven to slow progression of the disease to end-stage heart failure. Because RBM20-related DCM is associated with sudden death, detection of RBM20 mutations could contribute to risk stratification and the decision whether to implant a cardioverter-defibrillator (ICD) for primary prevention of sudden death.

This document also provides methods and materials to assist medical or research professionals in determining whether or not a mammal (e.g., a human) is likely to develop DCM and heart failure. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining whether a subject has a RBM20 sequence variant, and (2) communicating information about the RBM20 sequence variant to that professional.

In some embodiments, a method for assessing the likelihood that a subject will develop DCM can include receiving a biological sample obtained from the subject, assaying the sample to determine whether it contains a RBM20 sequence variant, communicating to a medical professional information about whether the RBM20 sequence variant is present in the sample, and, in some cases, before or after the first step, communicating to a medical professional information indicating that the presence of the sequence variant correlates with development of DCM.

After information regarding whether a subject has a RBM20 sequence variant is reported, a medical professional can take one or more actions that can affect patient care. For example, a medical professional can record the information in a subject's medical record. In some cases, a medical professional can record that the subject is likely or not likely to develop DCM, or otherwise transform the patient's medical record, to reflect the patient's medical condition. In some cases, a medical professional can review and evaluate a patient's medical record, and can assess multiple treatment strategies for clinical intervention of a patient's condition.

A medical professional can communicate information regarding RBM20 sequence analysis to a subject or a subject's family. In some cases, a medical professional can provide a subject and/or a subject's family with information regarding therapy for DCM, including treatment options and potential side effects or using an implantable cardioverter-defibrillator (ICD). In some cases, a medical professional can provide a copy of a subject's medical records to communicate information regarding RBM20 sequence analysis and/or disease states to a specialist.

In some cases, a medical professional can provide a subject or a subject's family with information regarding the likelihood of inheritance of the RBM20 sequence variant and the likelihood that family members will also develop DCM.

A research professional can apply information regarding a subject's RBM20 sequence variant to advance research into treatment for DCM. For example, a researcher can compile data on the presence of the RBM20 sequence variant with information regarding the efficacy of a therapy, or side effects associated with the therapy. In some cases, a research professional can determine whether a subject has the RBM20 sequence variant to evaluate the subject's enrollment, or continued participation in a research study or clinical trial. In some cases, a research professional can communicate whether a subject has the RBM20 sequence variant to a medical professional, or can refer a subject to a medical professional for clinical assessment and/or treatment.

Any appropriate method can be used to communicate information to another person (e.g., a professional), and information can be communicated directly or indirectly. For example, a laboratory technician can input biomarker information into a computer-based record. In some cases, information can be communicated by making a physical alteration to medical or research records. For example, a medical professional can make a permanent notation or flag a medical record for communicating information to other medical professionals reviewing the record. Any type of communication can be used (e.g., mail, e-mail, telephone, and face-to-face interactions). Information also can be communicated to a professional by making that information electronically available to the professional. For example, information can be placed on a computer database such that a medical professional can access the information. In addition, information can be communicated to a hospital, clinic, or research facility serving as an agent for the professional.

Articles of Manufacture

Articles of manufacture also are provided herein, and can include populations of isolated RBM20 nucleic acid molecules or RBM20 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different RBM20 nucleic acid or RBM20 polypeptide sequence variant. Such articles of manufacture can include two or more sequence variants of RBM20, or can include all of the sequence variants known for RBM20. For example, the article of manufacture can include one or more of the sequence variants identified herein and one or more other RBM20 sequence variants. Furthermore, nucleic acid molecules containing sequence variants for other DCM-related sequences can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al. (1996) *Nature Genet.* 14:441-447; and U.S. Pat. Nos. 5,770,772 and 5,733,729.

The invention will be further described in the following examples, which do not limit the scope of the invention described in the claims.

EXAMPLES

Example 1

Mutations in RBM20 Cause Familial DCM

Study Populations and Ascertainments:

Patients with DCM evaluated at the Mayo Clinic in the years 1987 to 1992 and 1999 to 2008 and their relatives were recruited, and medical records were reviewed. 280 unrelated probands were enrolled; familial DCM was confirmed in 24% (DCM documented in ≥1 first degree relative) and suspected in 27% (on the basis of history alone). Family history of sudden death was present in 18%. The 8 families described in the current study were white and of northern European ancestry by self-reporting. An ethnically matched group of 480 control subjects with normal echocardiograms was randomly selected from a community-based cohort (Redfield et al., *JAMA* 289:194-202 (2003)). This study was approved by the appropriate institutional review board and appropriate informed consent was obtained from all participants.

Echocardiograms in relatives were performed for clinical indications or under the auspices of the research study. Diagnostic criteria for DCM were: lack of an identifiable cause for disease, left ventricular diastolic and/or systolic dimensions >95th percentile indexed for body surface area (Henry, et al., *Circ.* 62:1054-1061 (1980)), and left ventricular ejection fraction <50%. Subjects with normal echocardiograms were classified as "unaffected," and those with equivocal or insufficient data were classified as "uncertain." Genomic deoxyribonucleic acid (DNA) was isolated from peripheral-blood white cells (Puregene Blood Kit, Gentra/QIAGEN, Valencia, Calif.) or from paraffin-embedded tissue (QJAamp DNA FFPE Tissue Kit, QIAGEN).

Linkage Analysis and Fine Mapping:

Genome-wide linkage analysis was performed with the ABI PRISM Linkage Mapping Set MD10, version 2.5 (Applied Biosystems, Foster City, Calif.), consisting of polymerase chain reaction (PCR) primer pairs for 400 short tandem repeat markers. After PCR amplification of DNA samples, fragments were resolved on an ABI PRISM 3130×1, and genotypes were scored with GeneMapper Software (Applied Biosystems). Two-point and multipoint linkage analyses were performed using the FASTLINK program and specification of the following variables: a phenocopy rate of 0.001, equal marker allele frequencies, and dichotomous liability classes ("affected" and "unaffected"). For mutations, a frequency of 0.001 was specified. Logarithm of the odds (LOD) scores were determined for affected subjects only and for 80% and 100% penetrance models at recombination frequencies of 0.0 to 0.4.

Fine locus mapping was performed with microsatellite markers on physical maps, accessible on the website of the National Center for Biotechnology Information (NCBI). Genotyping was accomplished by PCR amplification of DNA radiolabeled with [alpha$^{32}$P] deoxycytidine triphosphate, resolution of alleles by polyacrylamide-gel electrophoresis, and visualization by autoradiography. Scored genotypes were assembled as haplotypes to define the critical region.

Mutation Detection and Haplotype Analysis

Expression profiles of candidate genes, derived from Affymetrix GeneChip® array data for 12 normal human tissues (accession GDS424) or 61 normal mouse tissues (accession GDS592), were assessed by searching the Gene Expression Omnibus (GEO) link on the NCBI website. The genomic structure of RBM20 was based on predicted reference messenger ribonucleic acid (mRNA) sequence (accession NM_001134363.1), retrieved from NCBI. Primer pairs were designed for genomic DNA PCR-amplification of the coding regions of the 14 predicted exons (Table 1), with Oligo Primer Analysis Software, version 6.71 (Molecular Biology Insights, Cascade, Colo.). For sequencing, amplified products were treated with ExoSAP-IT (USB Corp., Cleveland, Ohio) and sequenced by the dye-terminator method with use of an ABI PRISM 3730×1 DNA Analyzer (Applied Biosystems). The DNA sequences were viewed and analyzed with Sequencher, version 4.5 DNA analysis software (Gene Codes Corp., Ann Arbor, Mich.). The reference mRNA and derived protein sequence (accession NP_001127835.1) were used for annotation of identified mutations.

Denaturing high-performance liquid chromatography (DHPLC) heteroduplex analysis (WAVE DHPLC System, Transgenomic, Omaha, Nebr.) was used to screen for sequence variants in our DCM cohort and control samples. Ideal buffer gradients and column melting temperatures were determined with Transgenomic Navigator software version 1.7.0 Build 25 and subsequent optimization (Table 1). PCR reactions contained final concentrations of 0.2 mmol/L AmpliTaq Gold PCR Buffer II (Applied Biosystems)+ dNTPs, 2.0 mmol/L MgCl$_2$, 0.4 µM forward and reverse primers respectively, 6.25 ng template DNA and 0.0125 U AmpliTaq Gold DNA Polymerase. Reactions began with a 10 minute hot start at 95° C. and cycled at 95° C. for 30 seconds, the indicated annealing temperature for 30 seconds and 72° C. extension for 30 seconds for 30 cycles. Reactions ended with a 72° C. 10 minute final extension step. The asterisk indicates Exon 1 reactions additionally included final concentrations of 0.3 mol/L betaine and 6% DMSO, and reactions were subjected to 40 cycles at the indicated annealing temperature. Exon 1 amplicons were electrophoresed, excised from a 3% agarose gel and extracted using the QIAquick Gel Extraction Kit (QIAGEN) according to manufacturer protocol prior to ExoSAP-IT treatment and automated sequencing.

Chromatographic elution profiles of amplified fragments were compared against the wild-type homoduplex pattern; samples yielding anomalous traces were selected for sequencing. To test for a common founder among families with the same RBM20 mutation, haplotypes for mutant alleles were constructed from an intragenic tetranucleotide-repeat sequence and single nucleotide polymorphisms, identified by sequencing family members.

TABLE 1

RBM20 PCR Primers and Conditions for Genomic DNA Sequence and Heteroduplex Analyses.

| Exon | Forward Primer (5'→3') | Reverse Primer (5'→3') | Annealing Temperatures (° C.) | DHPLC Melting Temperatures (° C.) |
|---|---|---|---|---|
| 1 | GGGAAGGACAAGGGGACTG (SEQ ID NO: 4) | AACAGCCAGAAGGACACCGACT (SEQ ID NO: 5) | 62* | 62.9 |
| 2.1 | CCAGCTGTGCATCTAGACC (SEQ ID NO: 6) | GCTTTGCCATACTCATAGAAT (SEQ ID NO: 7) | 58 | 62, 62.3 |
| 2.2 | TACCCGGTTTCCCTCTAATG (SEQ ID NO: 8) | GTTCCTCGGGGTCGTACAG (SEQ ID NO: 9) | 60 | 61.8 |
| 2.3 | CCCAACTCCCAAGGTTCAC (SEQ ID NO: 10) | CTCCCAGCCTGTCTTGGAC (SEQ ID NO: 11) | 58 | 62.7 |
| 3 | TCCCTGCCTGACCAGTGTC (SEQ ID NO: 12) | CTGTCCTCCTGAACAGCACTTA (SEQ ID NO: 13) | 62 | 59.9 |
| 4 | CCGGTTTCCCTTTCTCG (SEQ ID NO: 14) | GCTTTCTACATCCGTGAGA (SEQ ID NO: 15) | 54 | 59.2, 61.2 |
| 5 | CAGAGGTACAATCATGCCAATC (SEQ ID NO: 16) | CTTGGGACCAGGAGTTAGTTCA (SEQ ID NO: 17) | 64 | 52.8, 55.4, 57.8 |
| 6 | GTTTAGGGGAAAGATAGCCATTA (SEQ ID NO: 18) | ATCACCAGCAAAAACACCTACGC (SEQ ID NO: 19) | 64 | 58.3, 58.8, 60.8 |
| 7 | ATGCCTTGTGCTGAATCTTG (SEQ ID NO: 20) | AACACGGAGGAGAAACTCAT (SEQ ID NO: 21) | 58 | 56.3, 58.1 |
| 8 | CCCCACCCAGTTCAGCATTATA (SEQ ID NO: 22) | AGAACAGGGCACAGCATGACTC (SEQ ID NO: 23) | 66 | 57.3, 60.1, 61.9 |
| 9.1 | AGAGTTGGGAGTTAAGAGTGTA (SEQ ID NO: 24) | GCTGCTGCTTCAGATACTTGT (SEQ ID NO: 25) | 62 | 64.2 |
| 9.2 | AACTGGACAAGGCTGAGTTGGAC (SEQ ID NO: 26) | TGGGGAAGAAATTGATCATTAC (SEQ ID NO: 27) | 60 | 56.7, 62.8 |
| 10 | AGAGCTGGGACCTGCATTCAATA (SEQ ID NO: 28) | ATGTGGGTAAAGATCGCTTCA (SEQ ID NO: 29) | 60 | 57.5, 59.7 |
| 11.1 | TGATTTGAGTGGTCCTTATGGC (SEQ ID NO: 30) | CCAGGCATTTCCACGTCCATGT (SEQ ID NO: 31) | 64 | 59.7, 60.1 |
| 11.2 | AGAAATTGTGCCCATTGAC (SEQ ID NO: 32) | TGAGGAAGGGGAGATAGTTAC (SEQ ID NO: 33) | 54 | 57.6, 61, 61.4 |
| 12 | TGCCTTGGTTCATGTTTT (SEQ ID NO: 34) | CAAAATGCCAAAAGCTCTC (SEQ ID NO: 35) | 50 | 58.3 |
| 13 | TCAGTAACCAGCCAAGGTCAAC (SEQ ID NO: 36) | AGAGCAGCCTGATGGAATCAAG (SEQ ID NO: 37) | 66 | 58.3, 61.7 |

TABLE 1-continued

RBM20 PCR Primers and Conditions for Genomic DNA Sequence and Heteroduplex Analyses.

| Exon | Forward Primer (5'→3') | Reverse Primer (5'→3') | Annealing Temperatures (° C.) | DHPLC Melting Temperatures (° C.) |
|---|---|---|---|---|
| 14 | GATTGAGGCATGTCCG (SEQ ID NO: 38) | ACACCTGGGTGACTTGCT (SEQ ID NO: 39) | 50 | 60.3, 61.1, 62.7 |

Cardiac mRNA Expression and Protein Structure Analysis

Total RNA was extracted from frozen human heart tissue (RNeasy Fibrous Tissue Midi Kit, QIAGEN), and 1.0 µg was reverse transcribed with an oligo(dT) primer to produce complementary deoxyribonucleic acid (cDNA) from mRNA (SMART RACE cDNA Amplification Kit, Clontech, Mountain View, Calif.). Primers cDNA-F (CCTACCCCAGAT-CATCCAAAATGC; SEQ ID NO:40) and cDNA-R (AA-CAAACACTTTGCAGTCAGTTATACA; SEQ ID NO:41) were designed to PCR amplify and sequence 5'-RACE-Ready cDNA, spanning the RBM20 region containing the identified mutations. A subsequent nested reaction with primers cDNA-2F (GAACCCATTCTCGGTCAGTAACCC; SEQ ID NO:42) and cDNA-2F/3'UTR-R (TCTCTCTGCCCTTC-CTCCATTAGT SEQ ID NO:43) was performed to provide optimal sequence quality. The RBM20 reference protein sequence was subjected to a Conserved Domain Database search performed with BLASTP, accessed on the NCBI website, to identify conserved structural domains. Conservation of amino acids altered by RBM20 missense mutations was investigated by aligning our translated RBM20 cDNA sequence with RBM20 protein sequences of other species.

Results

Phenotype of Index Families

Clinical data and DNA samples were collected from 2 large families in which a clinically aggressive form of DCM segregated as an autosomal-dominant trait (FIG. 4A, FIG. 4B, Table 2). Kindred DC-12 was recruited for the study in 1991, when an unaffected family member sought medical genetics consultation. The patriarch (FIG. 4A: I.1) was of Scottish ancestry and died suddenly at age 39 years. Ten family members developed documented DCM, 2 as young children (mean age at diagnosis: 30.0 years). Two underwent cardiac transplantation as young adults, and all but 3 have died of their disease (mean age at death: 37.7 years). Kindred DC-35 was recruited in 2005, after a diagnostic screening echocardiogram in the proband (FIG. 4B: III.17) whose father died suddenly at age 29 years. The family was of Norwegian ancestry and comprised 12 relatives with documented DCM (mean age at diagnosis: 41.3 years) and 5 others with DCM and/or sudden death by history alone. Seven family members with confirmed or suspected DCM died at a mean age of 45.7 years. Five living relatives with DCM had received implantable cardioverter-defibrillators (ICDs).

DCM Locus Mapping

Genome-wide linkage analyses, followed by regional high-density genotyping on chromosome 10, identified a peak 2-point LOD score of 3.55 at marker D10S1269 in DC-12 and 4.55 at marker D10S221 in DC-35. Linkage to other regions of the genome with 2-point LOD scores >1.0 was excluded by multipoint and/or haplotype analyses with additional markers (data not shown). Fine mapping in DC-12 identified a disease-associated haplotype on chromosome 10q25.1-q26.2 (FIG. 4A), a region spanning 19.3 Mb, which was inherited by all affected subjects (peak multipoint LOD score 3.62 for all subjects, assuming 100% mutation penetrance, and 2.67 for affected subjects only). A recombination event within this interval occurred in a 43-year-old woman with a normal echocardiogram (III.14). The critical region narrowed to 4.6 Mb, assuming she did not inherit the disease-associated mutation. Fine mapping in DC-35 identified an overlapping disease-associated haplotype (FIG. 4B) spanning 22.8 Mb (peak multipoint LOD score 4.89 for all subjects, assuming 100% mutation penetrance, and 3.58 for affected subjects only). The haplotypes were different for each family, suggesting they did not share common ancestry, yet the overlapping disease loci raised the possibility of a shared DCM gene.

TABLE 2

Phenotypic and Genetic Data for Families With DCM.

| Pedigree (Country of Origin) | Age at Diagnosis (yrs) | Age at Evaluation (yrs) (Indication) | LVID (mm) | LVEF (%) | ECG, Arrhythmia | Other Diagnostic Testing | Treatment | Outcome | Pathology | Diagnosis | RBM20 Mutation Status |
|---|---|---|---|---|---|---|---|---|---|---|---|
| DC-12 (Scotland) | | | | | | | | | | | |
| II.5 | — | 58 (F) | 55/31 | 68 | Normal | | None | Alive 58 yrs | | Unaffected | Normal |
| II.9 | 53 | 53 (R) | 64*/53* | 39 | LVH, PVC | | D, F | Death 58 yrs | Autopsy: congestive myopathy, fibrosis, myocyte hypertrophy, no CAD | DCM | P638L |
| II.10 | 44 | 45 (S) | Severe LVE* | LVSD | AF, PVC | | | CHF, death 45 yrs | | DCM | P638L (inferred) |
| III.2 | 28 | 28 (S) | | | | | | SD 28 yrs | Autopsy: EFE, congestive myopathy, no CAD | DCM | P638L |
| III.3 | 37 | 37 (F) | 62*/57* | 15 | LAD, VT | Neg. angio | D, B | Death 41 yrs | Autopsy: mild fibrosis | DCM | P638L |
| III.5 | | 30 (R) | 40/24 | 64 | Normal | | | Death 38 yrs | Autopsy: normal LV and cardiac mass, no CAD | Uncertain (suspected arrhythmia) | Normal |
| III.8 | 30's | 36 (F) | 43/30 | 51 | Normal | | None | Alive 39 yrs | | Unaffected | Normal |
| III.9 | | 36 (S) | | | LBBB | | Transplant 36 yrs | Death 36 yrs | | DCM | P638L |
| III.11 | 33 | 33 (F) | 72*/62* | 26 | LVH, IVCD | | D, C | Alive 42 yrs | Autopsy: CM, mild fibrosis, no CAD | DCM | P638L |
| III.13 | 29 | 29 (S) | | | | | | SD 29 yrs | | DCM | P638L |
| III.14 | | 43 (F) | 51/36 | 50 | Normal | | None | Alive 46 yrs | | Unaffected | Normal |
| III.15 | 24 | 25 (F) | 88*/79* | 15 | LVH, IVCD | | Transplant 26 yrs | Death 27 yrs | | DCM | P638L |
| III.16 | 14 | 14 (F)→22 | 57*/41*  57*/41* | 48→ 45 | Short PR, SVT | | D, So | Alive 24 yrs | | DCM | P638L |
| IV.1 | 3 | 3 (F)→12 | 44*/30* 62*/40* | 50→ 64 | Short PR, LVH | | D, L | Alive 12 yrs | | DCM | P638L |
| DC-35 (Norway) | | | | | | | | | | | |
| III.1 | 55 | 55 (F) | 47/39* | 46 | PAC | Neg. stress imaging | | Alive 58 yrs | | DCM | R634Q |
| III.6 | 45 | 45 (S)→ 55 | 70*/→ 60*/50* | 10→ 30 | LAE, IVCD, ST-T | Neg. angio | D, Cv, L, Sp, W, ICD (EF, FH) | Alive 55 yrs | | DCM | R634Q |
| III.7 | | 60 (F) | 44/29 | 60 | Normal | | None | Alive 62 yrs | | Unaffected | Normal |
| III.8 | | 60 (F) | 39/29 | 60 | | | None | Alive 60 yrs | | Unaffected | Normal |
| III.9 | | 52 (F) | Normal | 65 | | | None | Alive 56 yrs | | Unaffected | Normal |
| III.10 | | 51 (HTN) | 44/28 | 67 | Normal | | None | Alive 52 yrs | | Unaffected | Normal |
| III.11 | 55 | 55 (S) | 72*/63* | 20 | Short PR, IVCD, ST-T, VT | | D, Cv, L, ICD (EF, FH, VT) | Alive 55 yrs | | DCM | R634Q |
| III.12 | 47 | 47 (A) | | | | | | Death 47 yrs | Autopsy: CM and LV dilation | DCM | R634Q |
| III.14 | 46 | 52 (F) | 63*/51* | 30 | | | ICD (EF, | Alive 52 yrs | | DCM | R634Q |

TABLE 2-continued

Phenotypic and Genetic Data for Families With DCM.

| Pedigree (Country of Origin) | Age at Diagnosis (yrs) | Age at Evaluation (yrs) (Indication) | LVID (mm) | LVEF (%) | ECG, Arrhythmia | Other Diagnostic Testing | Treatment | Outcome | Pathology | Diagnosis | RBM20 Mutation Status |
|---|---|---|---|---|---|---|---|---|---|---|---|
| III.15 | | 51 (F) | 54/27 | 55 | | | None | Alive 51 yrs | | Unaffected | Normal |
| III.17 | 48 | 48 (F) | 61*/44* | 45 | IVCD, ST-T, VT | Neg. angio | M, L, ICD (FH) | Alive 49 yrs | | DCM | R634Q |
| IV.1 | 50 | 50 (S) | 64*/55* | 20 | LAD, LAE, ST-T | Neg. angio | Cv, L | Alive 52 yrs | | DCM | R634Q |
| IV.2 | 37 | 37 (S) | Severe LVE* | 15 | LAE, LAD | Neg. angio, CK 102 u/l | D, E, W | CHF, death 37 yrs | Biopsy: myocyte hypertrophy, mild fibrosis | DCM | R634Q |
| IV.3 | | 44 (F) | 56*/36 | 65 | Normal | | None | Alive 48 yrs | | Uncertain | Normal |
| IV.4 | | 44 (F) | 51/32 | 52 | Normal | | None | Alive 46 yrs | | Unaffected | Normal |
| IV.5 | 40 | 40 (F) | 56*/43* | 40 | Normal | Neg. stress imaging; CK 70 u/l, cTnI <0.3 ng/ml | M, L | Alive 44 yrs | | DCM | R634Q |
| IV.6 | | 24 (F) | 54*/35 | 58 | Normal | Neg. stress imaging | None | Alive 27 yrs | | Uncertain | R634Q |
| IV.7 | | 23 (F) | 39/27 | 65 | Normal | | None | Alive 23 yrs | | Unaffected | Normal |
| IV.8 | 18 | 18 (F) | 61*/51* | 37 | IVCD, LVH | Neg. angio | Cv, L, ICD (FH, EF) | Alive 19 yrs | | DCM | R634Q |
| IV.9 | 30 | 30 (R) | 63*/45* | 42 | Normal | | | Alive 30 yrs | | DCM | R634Q |
| IV.10 | 24 | 24 (R) | 59/46* | 45 | LVH | | | Alive 24 yrs | | DCM | R634Q |
| DC-50 (Germany) | | | | | | | | | | | |
| II.3 | 49 | 52 (S) → 60 | 68*/62*→ 71*/65* | 17→ 15 | LVH, ST-T, AF, VT, VF | Neg. angio, CK 29 u/l, cTnI <0.5 ng/ml | D, F, P, C, A, W, ICD (Sy, FH) | CHF, death 60 yrs | Autopsy: sev. CM, mild fibrosis | DCM | P638L |
| II.5 | 29 | 29 (S) | | | ST-T, VT, VF | CK 29 u/l | D, P, PC | CHF, death 29 yrs | | DCM | P638L (inferred) |
| III.3 | 25 | 25 (R) → 42 | 55*/45*→ 51/— | 33→ 40 | LVH | | D, Cv, L | Alive 42 yrs | | DCM | P638L |
| III.4 | 29 | 29 (R) → 44 | 45/35→ 52/38* | 40→ 49 | ST-T | | Cv, E | Alive 44 yrs | | DCM | P638L |
| III.5 | 15 | 15 (S) | 75*/68* | 18 | LVH, ST-T, VT | | D, L, W, N, Mx | CHF, SD 18 yrs | Biopsy: myocyte hypertrophy, mild fibrosis | DCM | P638L |
| III.6 | | 29 (R) | 51/28 | 70 | Normal | | None | Alive 46 yrs | | Unaffected | Normal |
| III.7 | | 27 (R) | 50/32 | 60 | Normal | | None | Alive 36 yrs | | Unaffected | Normal |
| III.8 | 21 | 27 (R)→ 37 | 54*/40*→ 56*/46* | 51→ 35 | Short PR, SVT | | Cv, L | Alive 38 yrs | | DCM | P638L |
| IV.1 | 17 | 17 (S) | 51/40* | 40 | LVH, SVT | | M, E | Alive 22 yrs | | DCM | P638L |
| DC-46 (Germany) | | | | | | | | | | | |
| IV.1 | 26 | 18 (F)→ 26 | 53/36→ 56*/46* | 58→ 30 | ST-T | cTnT <0.03 ng/ml | Cv, L, ICD (EF, FH) | Alive 27 yrs | | DCM | R636S |

TABLE 2-continued

Phenotypic and Genetic Data for Families With DCM.

| Pedigree (Country of Origin) | Age at Diagnosis (yrs) | Age at Evaluation (yrs) (Indication) | LVID (mm) | LVEF (%) | ECG, Arrhythmia | Other Diagnostic Testing | Treatment | Outcome | Pathology | Diagnosis | RBM20 Mutation Status |
|---|---|---|---|---|---|---|---|---|---|---|---|
| DC-49 (Germany) | | | | | | | | | | | |
| II.2 | 40 | 40 (S)→45 | 71*/64*→65*/52* | 10→20 | LVH, ST-T, IVCD, VT | | D, M, L, Sp, F, W, Mx, ICD (CA) | Alive 45 yrs | | DCM | R636H |
| II.3 | 39 | 39 (F)→44 | 63*/49*→52/42 | 43→45 | VT | Neg. angio | Cv, Rm, Cn | Alive 44 yrs | | DCM | R636H |
| DC-27 (Norway) | | | | | | | | | | | |
| II.6 | 70 | 80 (S) | 63*/— | 25 | SB, AF | | D, Cv, L, F, W | CHF, death 85 yrs | | DCM | R636S |
| II.2 | | 64 (F) | 55*/40* | 50 | IRBBB | | Cv | Alive 64 yrs | | Uncertain | R636S |
| II.3 | 59 | | | | | | None | SD 59 yrs | Autopsy: CM, LVE, CAD but no acute MI, fibrosis | DCM | R636S (inferred) |
| III.5 | 55 | 59 (F) | 59*/44* | 44 | 1° AVB, RBBB, VT | Neg. angio | Cv | Alive 60 yrs | | DCM | R636S |
| III.8 | | 50 (F) | 45/— | 60 | Normal | | None | Alive 55 yrs | | Unaffected | Normal |
| III.10 | | 39 (F) | 54/38* | 55 | | | None | Alive 47 yrs | | Uncertain | R636S |
| IV.1 | 35 | 35 (S) | 68*/55* | 38 | LVH, ST-T, LAD, IVCD, ST-T | Neg. angio | Cv, L | Alive 36 yrs | | DCM | R636S |
| IV.5 | 27 | 36 (S) | 72*/65* | 23 | | Neg. angio | Cv, Ln | Alive 37 yrs | Biopsy: myocyte hypertrophy, mod. fibrosis | DCM | R636S |
| IV.7 | | 28 (R) | 50/33 | 66 | Normal | | None | Alive 31 yrs | | Unaffected | Normal |
| IV.9 | | 15 (F) | 52*/34 | 57 | Normal | | None | Alive 18 yrs | | Uncertain | R636S |
| DC-09 (Norway) | | | | | | | | | | | |
| III.2 | 57 | 57 (R)→68 | 58*/46*→59*/49* | 35→34 | Short PR, PVC | | D, E, F, A | Alive 68 yrs | | DCM | R636S |
| III.4 | | | | | | Neg. angio | | Alive 68 yrs | | DCM (by history) | R636S |
| IV.2 | 17 | 17 (S) | 68*/60* | 22 | LVH, ST-T | | D, H, N, F, W | CHF, SD 18 yrs | | DCM | R636S |
| IV.3 | | 27 (R) | 50/32 | 60 | Normal | | None | Alive 38 yrs | | Unaffected | Normal |
| IV.4 | | 24 (R) | 53/33 | 61 | Normal | | None | Alive 36 yrs | | Unaffected | Normal |
| IV.6 | 19 | 20 (S) | | | | | Transplant 20 yrs | Alive 43 yrs | | DCM | R636S |
| DC-22 (England) | | | | | | | | | | | |
| II.2 | 44 | 45 (S) | 53*/44* | 25 | ST-T, VT | Neg. angio | D, F, A, Cv, Ln, ICD (EF, FH) Transplant 32 yrs | CHF, alive 54 yrs | | DCM | S637G |
| II.3 | 27 | 27 (S) | | | | | | Alive 49 yrs | | DCM | S637G |

TABLE 2-continued

Phenotypic and Genetic Data for Families With DCM.

| Pedigree (Country of Origin) | Age at Diagnosis (yrs) | Age at Evaluation (yrs) (Indication) | LVID (mm) | LVEF (%) | ECG, Arrhythmia | Other Diagnostic Testing | Treatment | Outcome | Pathology | Diagnosis | RBM20 Mutation Status |
|---|---|---|---|---|---|---|---|---|---|---|---|
| III.1 | 21 | 21 (F) | 53*/39* | 35 | ST-T | Neg. stress imaging | Cv, L | Alive 28 yrs | | DCM | S637G |
| III.2 | 20 | 20 (F) | 48/34* | 46 | Short PR | | Cv | Alive 23 yrs | | DCM | S637G |

Indication for evaluation:
A = autopsy;
F = family history;
HTN = hypertension;
S = symptoms;
R = research study.
Echocardiography:
LVE = left ventricular enlargement;
LVEF = left ventricular ejection fraction (normal ≥50%);
LVID = left ventricular internal dimension in diastole/systole;
LVSD = left ventricular systolic dysfunction.
Electrocardiogram, arrhythmia:
AF = atrial fibrillation;
1° AVB = first degree atrioventricular block;
IRBBB = incomplete right bundle branch block;
IVCD = intraventricular conduction delay;
LAD = left axis deviation;
LAE = left atrial enlargement;
LBBB = left bundle branch block;
LVH = left ventricular hypertrophy;
PAC = premature atrial contractions;
PR = PR interval;
PVC = premature ventricular contractions;
SB = sinus bradycardia;
ST-T = nonspecific ST-T wave changes;
SVT = supraventricular tachycardia;
VF = ventricular fibrillation;
VT = ventricular tachycardia.
Other diagnostic testing:
CK = creatine kinase;
cTnI = cardiac troponin I;
cTnT = cardiac troponin T;
Neg. angio = no significant coronary artery disease on angiography.
Treatment:
A = amiodarone;
B = benazepril;
C = captopril;
Cn = candesartan;
Cv = carvedilol;
D = digoxin;
E = enalapril;
F = furosemide;
H = hydralazine;

TABLE 2-continued

Phenotypic and Genetic Data for Families With DCM.

| Pedigree (Country of Origin) | Age at Diagnosis (yrs) | Age at Evaluation (yrs) (Indication) | LVID (mm) | LVEF (%) | ECG, Arrhythmia | Other Diagnostic Testing | Treatment | Outcome | Pathology | Diagnosis | RBM20 Mutation Status |
|---|---|---|---|---|---|---|---|---|---|---|---|

ICD = implantable cardioverter-defibrillator;
L = lisinopril;
Ln = losartan;
M = metoprolol;
Mx = mexiletine;
N = nitroglycerin;
P = propranolol;
PC = procainamide;
Rm = ramipril;
So = sotalol;
Sp = spironolactone;
Transplant = cardiac transplantation;
W = warfarin.
Indication for ICD (in parentheses):
CA = cardiac arrest;
EF = ejection fraction;
FH = family history;
Sy = syncope;
VT = ventricular tachycardia.
Outcome:
CHF = congestive heart failure;
SD = sudden death.
Pathology:
CAD = coronary artery disease;
CM = cardiomegaly;
EFE = endocardial fibroelastosis;
MI = myocardial infarction;
mod. = moderate;
Sev. = severe.
*Left ventricular internal dimension measurement in diastole/systole >95th percentile, on the basis of body surface area and age.

Mutation Identification

Candidate genes were selected from the 19.3-Mb critical region in DC-12, comprising more than 150 genes, on the basis of cardiac expression and/or physiologic rationale. Mutations within exons of 25 genes were excluded by DNA sequencing (Table 3). RBM20, a gene with unknown function, was included on the basis of its genomic location and expression pattern. Among 12 human tissues, RBM20 is most highly expressed in the heart, with transcript abundance 4-fold greater in cardiac than in skeletal muscle according to GEO array data. Moreover, it is 1 of only 19 genes with a mean expression in the heart >8-fold higher than the combined mean expression in 11 other tissues. Similarly, among 61 murine tissues it is most highly expressed in heart (>5-fold skeletal muscle). Sequencing of the 14 exons of RBM20 identified a distinct heterozygous missense mutation in exon 9 in each family, resulting in a P638L substitution in DC-12 and a R634Q substitution in DC-35 (FIG. 1 and FIG. 3A). Mutations cosegregated with the disease phenotype and were absent in unaffected family members and 480 ethnically matched control subjects.

Figure 5:
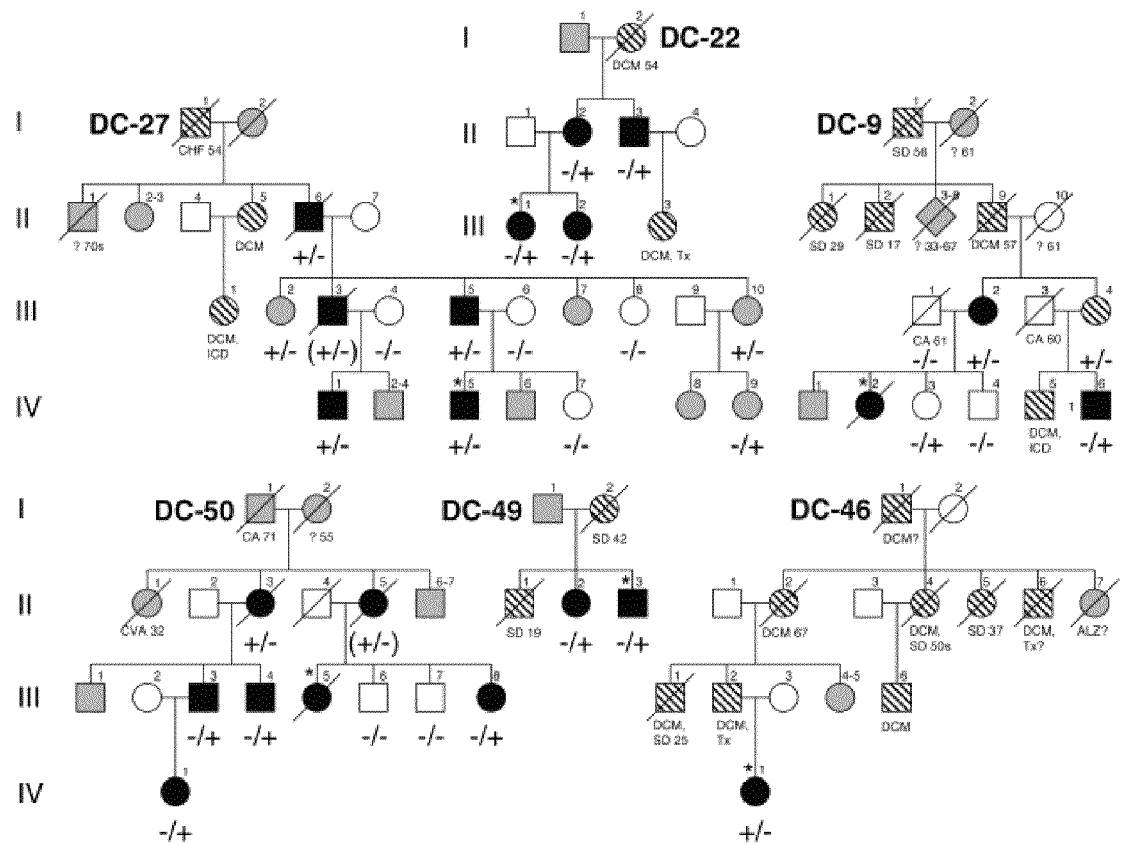
FIG. 5 is a diagram of the pedigrees of six additional DCM families with RBM20 mutations. Diamonds=two or more family members of both sexes; parentheses=inferred RBM20 mutation status. Other symbols and abbreviations are as defined in the description of FIG. 4.
Figure 6:
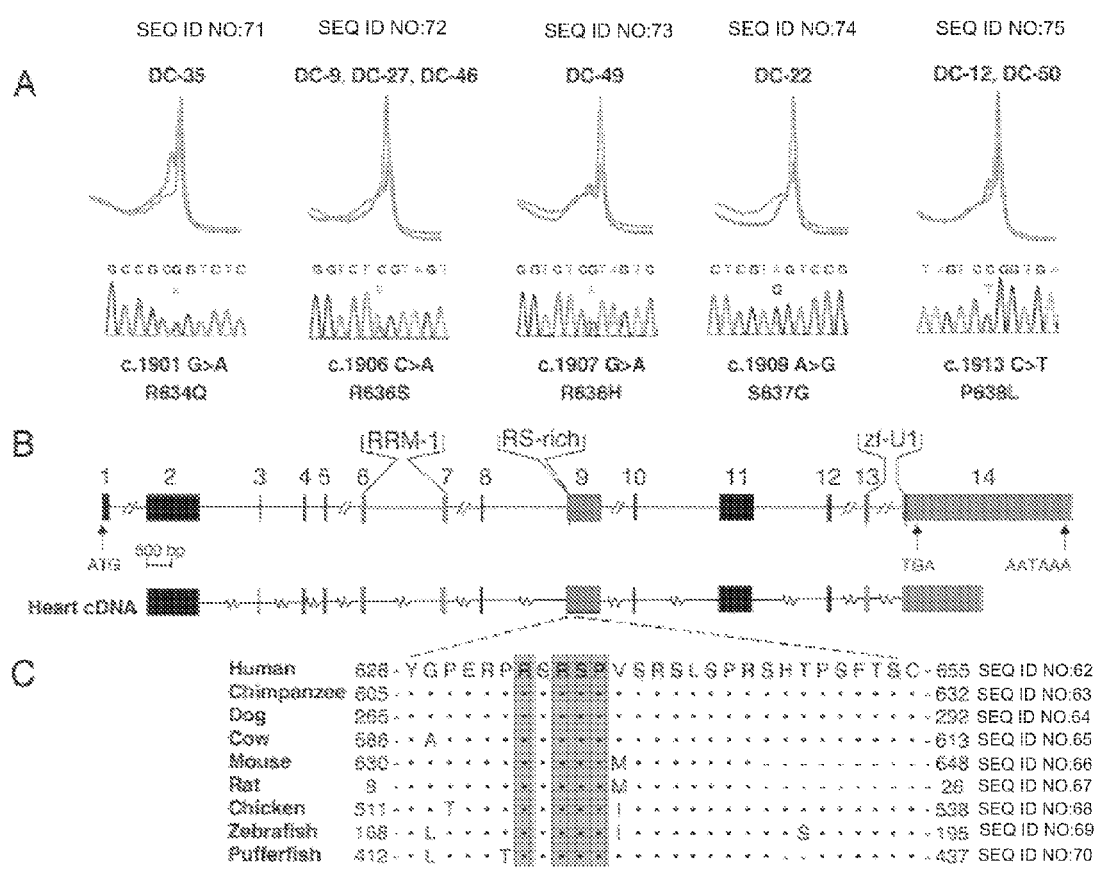
FIG. 6A is mutation scans in exon 9 of RBM20 in 8 DCM families using denaturing high-performance liquid chromatography (DHPLC). As compared to the control wild-type profile (gray), samples from DCM families were abnormal heteroduplex profiles, indicating DNA sequence alterations. Below the heteroduplex profiles, DNA sequencing revealed corresponding heterozygous missense mutations. The location of each mutation and its resultant amino acid substitution are based on predicted reference RBM20 complementary deoxyribonucleic acid (cDNA) and protein sequences and are indicated below each chromatogram. Mutation c.1906 C>A, R636S was shared by three families, and c.1913 C>T, P638L was shared by two families.
FIG. 6B represents the predicted genomic structure of RBM20, consisting of 14 exons and is depicted to scale. Exons that encode peptides homologous to highly conserved functional domains—ribonucleic acid (RNA) recognition motif 1 (RRM-1), arginine/serine-rich region (RS-rich), and U1 zinc finger (zf-U1)—are indicated. Putative start (ATG) and stop (TGA) codons are located in exons 1 and 14, respectively. A polyadenylation signal (AATAAA) is located at the 3' end of exon 14. Directly below the RBM20 genomic structure, cDNA amplification and sequencing confirmed transcription of messenger RNA from exons 2 to 14 in human heart tissue, as depicted by parallel alignment. The cDNA transcript contains the complete RS domain and identified RBM20 mutations in the 5' region of exon 9.
FIG. 6C contains alignments of homologous RBM20 protein sequences that flank the amino acid substitutions. The RS domain spans residues 632 to 654, with arginine (R) and serine (S) residues indicated. Residues conserved between human RBM20 and another species are indicated by (●) and amino acid deletions by (–). Amino acids that are altered by the identified RBM20 missense mutations (residues 634, 636, 637, and 638, indicated with shading) are conserved among all eight species. Accession numbers: NP_001127835.1 (GI No. 197276594) for human, XP_50832 (GI No. 114632917) for chimpanzee, XP_544017 (GI No. 57107611) for dog, XP_603772 (GI No. 194678822) for cow, BAE24961 (GI No. 74209138) for mouse, NP_001101081 (GI No. 255982592) for rat, XP_421755 (GI No. 118093031) for chicken, XP_683222 (GI No. 125851038) for zebrafish, and CAG01297 (GI No. 47214762) for pufferfish.

To determine whether RBM20 mutations were present in other cases of DCM, the 14 coding exons in the remaining cohort of 278 subjects were screened using DHPLC. Three unique heterozygous missense mutations—R636S, R636H, and S637G—were identified in 6 other families, all clustered within exon 9 (FIG. 5 and FIG. 6A). Among the 8 families with RBM20 mutations, 2 had an identical mutation resulting in P638L substitution, and 3 had an identical mutation resulting in R636S substitution. Haplotype analysis (Tables 4A and 4B) excluded a common ancestral founder for the P638L substitution. These tables list the genotypes in order from the 5' to 3' ends of the gene and identified mutations within exon 9 are also indicated. The alleles that comprise the disease-associated haplotype are indicated by underlined and bold font. In Table 4B, frequency data for the shared allele in a White European population sample are shown following the SNP accession number (accessed from the SNP link on the NCBI Web site). Although the disease-associated haplotypes were the same in the 3 families with an R636S substitution, the majority of individual alleles comprising the haplotype are the most common variants within a white European population. Consequently, a founder effect could not be conclusively established. Mutations were absent in control samples and cosegregated with DCM in the 7 families where DNA samples were available from 2 or more affected subjects. Combined peak 2-point LOD scores for mutations versus DCM in the 4 largest families (DC-12, DC-35, DC-27, DC-50) ranged from 8.02 (affected subjects only) to 11.49 (all subjects, assuming 100% mutation penetrance).

TABLE 3

Candidate Genes at 10q26 Locus Excluded by Genomic DNA Sequencing.

| Symbol | Description | Chromosome location (bp) | Family |
|---|---|---|---|
| XPNPEP1 | X-prolyl aminopeptidase (aminopeptidase P) 1, soluble | 111614514-111673192 | 12 |
| ADD3 | adducin 3 (gamma) | 111755716-111885313 | 12 |
| MXI1 | MAX interactor 1 | 111957353-112037113 | 12 |
| SMNDC1 | survival motor neuron domain containing 1 | 112042788-112054687 | 12, 35 |
| DUSP5 | dual specificity phosphatase 5 | 112247615-112261292 | 12, 35 |
| PDCD4 | programmed cell death 4 (neoplastic transformation inhibitor) | 112621586-112649754 | 12 |
| SHOC2 | soc-2 suppressor of clear homolog (*C. elegans*) | 112713903-112763413 | 12, 35 |
| ADRA2A | adrenergic, alpha-2A-, receptor | 112826911-112830560 | 12 |
| GPAM | glycerol-3-phosphate acyltransferase, mitochondrial | 113899612-113933508 | 12 |
| ACSL5 | acyl-CoA synthetase long-chain family member 5 | 114123906-114178128 | 12 |
| VTI1A | vesicle transport through interaction with t-SNAREs homolog 1A (yeast) | 114196746-114568493 | 12, 35 |
| ADRB1 | adrenergic, beta-1-, receptor | 115793796-115796657 | 12 |
| ABLIM1 | actin binding LIM protein 1 | 116180859-116344404 | 12 |
| PNLIP | pancreatic lipase | 118295418-118317357 | 12, 35 |
| HSPA12A | heat shock 70 kDa protein 12A | 118420693-118492075 | 12, 35 |
| KCNK18 | potassium channel, subfamily K, member 18 | 118946990-118959800 | 12, 35 |
| SLC18A2 | solute carrier family 18 (vesicular monoamine), member 2 | 118990706-119027085 | 12 |
| PRDX3 | peroxiredoxin 3 | 120917205-120928335 | 12, 35 |
| GRK5 | G protein-coupled receptor kinase 5 | 120957187-121205121 | 12, 35 |
| RGS10 | regulator of G-protein signaling 10 | 121249329-121292212 | 12 |
| BAG3 | BCL2-associated athanogene 3 | 121400872-121427321 | 12, 35 |
| ATE1 | arginyltransferase 1 | 123492615-123677536 | 12, 35 |
| TACC2* | transforming, acidic coiled-coil containing protein 2 | 123738679-124004047 | 12, 35 |
| PLEKHA1 | pleckstrin homology domain containing, family A (phosphoinositide binding specific) member 1 | 124124210-124181856 | 12, 35 |
| ADAM12* | ADAM metallopeptidase domain 12 (meltrin alpha) | 127693415-128067055 | 12 |

TABLE 4A

RBM20 Haplotypes for P638L Substitution.

| | DC-12 | | | DC-50 | |
|---|---|---|---|---|---|
| RBM20 Variant | II.9 | III.15 | II.11 | II.3 | III.2 |
| Intron 2 + 34 (ENSSNP311449; SEQ ID NO: 44) | T/C | C/C | T/T | T/T | C/T |
| Intron 2 + 36 (ENSSNP10311387; SEQ ID NO: 45) | G/A | A/A | G/G | G/G | A/G |

TABLE 4A-continued

RBM20 Haplotypes for P638L Substitution.

| | DC-12 | | | DC-50 | |
| --- | --- | --- | --- | --- | --- |
| RBM20 Variant | II.9 | III.15 | II.11 | II.3 | III.2 |
| Intron 5 (TCTA)-repeat (rs10554324; SEQ ID NO: 46) | 2/2 | 1/2 | | 1/1 | 2/1 |
| Intron 8 + 23 (rs11195338; SEQ ID NO: 47) | T/C | C/C | | T/T | C/T |
| Exon 9 c.1913 (mutation) | C > T | C > T | C/C | C > T | C > T |
| Exon 14 + 94 (rs942077; SEQ ID NO: 48) | C/G | C/G | C/C | C/C | C/C |

TABLE 4B

RBM20 Haplotypes for R636S Substitution.

| | DC-27 | | | | DC-46 | DC-9 | | |
| --- | --- | --- | --- | --- | --- | --- | --- | --- |
| RBM20 Variant | III.5 | IV.5 | III.6 | II.6 | IV.1 | III.2 | IV.3 | III.1 |
| Intron 3 + 32 (rs6585012; SEQ ID NO: 49; 0.78) | A/A | A/A | | | G/A | G/A | A/A | |
| Intron 3 + 160 (rs1570426; SEQ ID NO: 50; 0.89) | A/G | G/G | | | G/G | G/G | G/G | |
| Intron 3-36 (rs7898438; SEQ ID NO: 51; 0.58) | A/C | C/C | | | A/C | A/C | C/C | |
| Intron 5 + 8 (rs7077757; SEQ ID NO: 52; 0.78) | T/C | C/C | | | C/C | C/C | C/C | |
| Intron 5 (TCTA)-repeat (rs10554324; SEQ ID NO: 53) | 1/1 | 1/1 | | | 1/1 | 1/1 | 2/1 | |
| Intron 6 + 108 (rs6585014; SEQ ID NO: 54; 0.12) | C/T | C/T | C/C | C/T | C/T | C/T | C/T | C/C |
| Intron 6-131 (rs7086886; SEQ ID NO: 55; 0.74) | A/G | G/G | | | G/G | A/G | G/G | |
| Intron 8 + 23 (rs11195338; SEQ ID NO: 56; 0.42) | T/C | T/C | C/T | C/C | T/C | C/C | C/C | |
| Exon 9 c.1906 (mutation) | C > A | C > A | C/C | C > A | C > A | C > A | C > A | C/C |

Cardiac mRNA Expression and Protein Structure Analysis

RBM20 comprises, on the basis of the predicted reference cDNA (mRNA), 14 exons (FIG. 6B). Portions of exons 2 and 14 and all of exons 3 through 13 were verified in a single open reading frame cDNA derived from oligo(dT)-primed heart RNA (FIG. 6B). This confirmed that these exons are transcribed and spliced into mRNA in the heart, including exon 9, which contained the cluster of identified RBM20 mutations. A Conserved Domain Database search of the translated reference RBM20 cDNA indicated homology to an RNA Recognition Motif 1 Superfamily domain spanning exons 6 and 7 (e-value=0.005) and a U1 zinc finger domain (e-value=$2e^{-4}$) spanning exons 13 and 14. Additionally, exon 9 encodes an arginine/serine (RS)-rich domain, which is disrupted by the 5 identified unique missense mutations. Each resultant amino acid substitution alters a residue in RBM20 conserved among diverse species (FIG. 6C).

Genotype Phenotype Correlation

RBM20 mutations were associated with clinically aggressive DCM. Collectively, the 39 subjects in our 8 families with a mutation and confirmed DCM were diagnosed 9 years earlier than a comparable series of patients with sporadic and familial DCM who underwent family screening (mean age at diagnosis 35.9 vs. 45.2 years) (Michels et al., N. Engl. J. Med. 326:77-82 (1992)). Death occurred in 11 (mean age 45.2 years) and was deemed sudden in 3; 4 underwent cardiac transplantation (mean age 28.5 years); and 8 underwent insertion of an implantable cardioverter-defibrillator (ICD). Subjects who enrolled in our study, however, did not fully represent the malignant nature of their familial disease as revealed by their pedigrees. Among the 32 additional relatives with suspected DCM by family history, for whom medical records were unavailable and/or mutation status could not be determined, 13 died suddenly (mean age 32.7 years), 3 underwent cardiac transplantation, and 3 had ICD insertion. There were no consistent electrocardiographic features in subjects with an RBM20 mutation; 9 had ventricular tachycardia. Variable degrees of myocyte hypertrophy and interstitial fibrosis were observed on histopathological analysis. Most enrolled subjects with accessible follow-up data had advanced disease and exhibited minimal improvement or further deterioration on medical treatment, although drug therapy was highly variable. Correlation between RBM20 mutations and phenotype was not without exception, however. There were 5 female subjects who inherited a mutation but did not fulfill diagnostic criteria for DCM: 1 subject in DC-35 (age 24 years) and 3 subjects in DC-27 (ages 15, 39, and 64 years) had left ventricular enlargement with normal ejection fraction; 1 subject in DC-9 (age 27 years) had a normal echocardiogram. No overt noncardiac phenotypes were evident among subjects with RBM20 mutations.

CONCLUSION

Five unique RBM20 mutations identified in 8 families are clustered within a single exon that encodes an RS-rich domain and were associated with clinically aggressive DCM. In the cohort, this mutation hotspot accounted for 3% (8 of 280) of all DCM cases, 5% (8 of 151) of confirmed or suspected familial cases, and 13% (7 of 54) cases with a history of sudden death. This study identified 68% of the subjects in eight families who were asymptomatic and first diagnosed with DCM on the basis of a screening echocardiogram, highlighting the importance of family screening. Despite the lack of symptoms, the identified RBM20 mutations were highly penetrant, and only 5 of 44 individuals with a mutation did not fulfill diagnostic criteria for DCM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion nucleic acid comprising a ribonucleic acid binding motif protein 20 (RBM20) nucleic acid sequence encoding a fragment of a RBM20 polypeptide that is 22 to 100 amino acid residues in length and a nucleic acid sequence heterologous to said RBM20 nucleic acid sequence, wherein said fragment of said RBM20 polypeptide comprises a mutation with respect to a reference sequence, wherein said reference sequence is set forth in SEQ ID NO:3, wherein said mutation is selected from the group consisting of Arg636Ser and Arg636His, and wherein said RBM20 nucleic acid sequence is separated from nucleic acids that normally flank both sides of said RBM20 nucleic acid sequence in the human genome.

2. The fusion nucleic acid of claim 1, wherein said nucleic acid sequence heterologous to said RBM20 nucleic acid sequence is a nucleic acid sequence encoding a tag.

* * * * *